United States Patent [19]
Muller et al.

[11] 4,024,249
[45] May 17, 1977

[54] HETEROARYLACETAMIDO CEPHALOSPORIN

[75] Inventors: Beat Müller, Reinach; Heinrich Peter, Binningen; Peter Schneider, Basel; Hans Bickel, Binningen, all of Switzerland

[73] Assignee: Ciba-Geigy Corporation, Ardsley, N.Y.

[22] Filed: Mar. 24, 1975

[21] Appl. No.: 561,444

Related U.S. Application Data

[63] Continuation-in-part of Ser. No. 451,262, March 14, 1974, abandoned.

[30] Foreign Application Priority Data

Mar. 30, 1973 Switzerland .............. 4608/72
Aug. 21, 1974 Switzerland ............ 11437/74

[52] U.S. Cl. .................... 260/243 C; 424/246
[51] Int. Cl.$^2$ ............................. C07D 501/20
[58] Field of Search ............ 260/243 C; 424/246

[56] References Cited
UNITED STATES PATENTS 3,382,241  5/1968  Flynn ........................ 260/243 C
3,488,730  1/1970  Stephens ................... 260/243 C

*Primary Examiner*—Nicholas S. Rizzo
*Attorney, Agent, or Firm*—Joseph G. Kolodny; John J. Maitner; Theodore O. Groeger

[57] ABSTRACT

Novel aminomethyl compounds of the formula

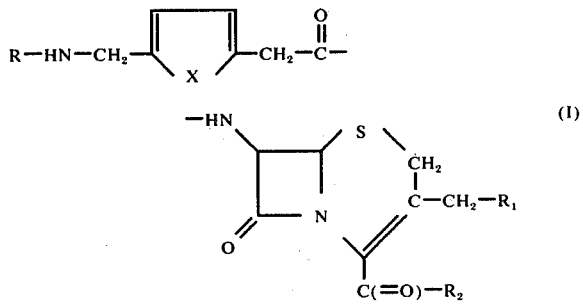

wherein X denotes sulphur or oxygen, R denotes hydrogen or an amino protective group, $R_1$ denotes hydrogen, a free, etherified or esterified hydroxyl group or mercapto group or a substituted ammonium group, $R_2$ denotes hydroxyl or a carboxyl protective radical which together with the carbonyl grouping of the formula -C(=O)- forms a protected carboxyl group, and their salts, are antibacterial antibiotics or intermediates for the preparation thereof; pharmaceutical preparations containing such active compounds, are useful for combating micro-organisms such as gram-positive or gram-negative bacteria; An illustrative example is 3-acetoxymethyl-7β-[2-(5-aminomethyl-2-thienyl)-acetylamino]-ceph-3-em-4-carboxylic acid.

8 Claims, No Drawings

HETEROARYLACETAMIDO CEPHALOSPORIN

CROSS REFERENCE

This is a continuation-in-part of our application Ser. No. 451.262, filed March 14, 1974.

The present invention relates to aminomethyl compounds, especially 7β-acylamino-ceph-3-em-4-carboxylic acid compounds of the formula

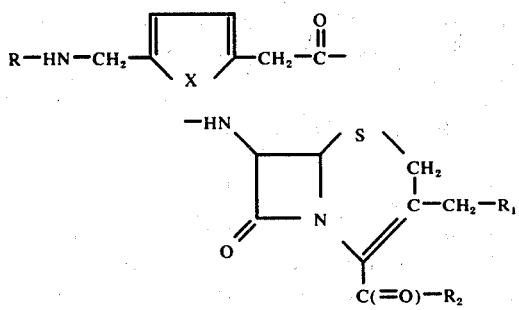

(I)

wherein X denotes sulphur or oxygen, R denotes hydrogen or an amino protective group, $R_1$ denotes hydrogen, a free, etherified or esterified hydroxyl group or mercapto group or a substituted ammonium group, $R_2$ denotes hydroxyl or a carboxyl protective radical which together with the carbonyl grouping of the formula —C(=O)— forms a protected carboxyl group, and their salts, and also processes for their manufacture as well as pharmaceutical preparations containing such compounds, and the use of such pharmaceutical preparations.

An amino protective group R is any of the easily removable amino protective groups known in peptide chemistry or in penicillin or cephalosporin chemistry. Such protective groups can be, for example, acyl, arylmethyl, 2carbonyl-1-vinyl, arylthio or aryl-lower alkylthio groups and also arylsulphonyl groups as well as organic silyl or stannyl groups.

An easily removable acyl group is, for example, the formyl group or the acyl radical of a half-ester of carbonic acid such as a lower alkoxycarbonyl group which, preferably on the carbon atom in the α-position to the oxy group, carries several aliphatic substituents or is branched and/or carries aromatic or heteroaromatic substituents, or a methoxycarbonyl group which is substituted by an arylcarbonyl radical, especially by a benzoyl radical, or a lower alkoxycarbonyl group which is substituted by halogen in the β-position, for example tert.-butoxycarbonyl, tert.-pentoxycarbonyl, phenacyloxycarbonyl, 2,2,2-trichloroethoxycarbonyl or 2-iodoethoxycarbonyl or a group which can be converted into the latter, such as 2-chloroethoxycarbonyl or 2-bromoethoxycarbonyl, and also preferably polycyclic cycloalkoxycarbonyl, for example adamantyloxycarbonyl, phenyl-lower alkoxycarbonyl which is optionally substituted, for example, by lower alkyl, hydroxyl, lower alkoxy or nitro, especially α-phenyl-lower alkoxycarbonyl, for example 4-methoxy-benzyloxycarbonyl, 4-hydroxy-3,5-bis-tert.-butyl-benzyloxycarbonyl, 4-nitrobenzyloxycarbonyl or α-4-biphenylyl-α-methylethyloxycarbonyl and also diphenylmethoxycarbonyl which is optionally substituted, for example by lower alkoxy, for example bis-(p-methoxyphenyl)-methoxycarbonyl, or furyl-lower alkoxycarbonyl, above all α-furyl-lower alkoxycarbonyl, for example furfuryloxycarbonyl. An acyl group for protecting the amino group can also be the corresponding radical of a suitable carboxylic acid, such as the phthaloyl or trifluoroacetyl radical.

Easily removable arylmethyl groups which should be singled out are, for example, benzyl or optionally substituted polyarylmethyl, such as triarylmethyl, groups, for example trityl optionally substituted by lower alkoxy, especially by o- and/or p-methoxy.

Easily removable 2-carbonyl-1-vinyl groups which together with the amino group form either an enamine or the ketimine tautomeric therewith are, for example, 2-lower alkoxycarbonyl-1-lower alkylvinyl groups, especially the 2-methoxycarbonyl-1-methyl-1-vinyl group.

Easily removable arylthio or aryl-lower alkylthio groups are, for example, substituted phenylthio groups, for example phenylthio groups substituted by nitro or halogen, such as the o-nitrophenylthio, the 2,4-dinitrophenylthio or the pentachlorophenylthio group, and also triarylmethylthio groups, for example the triphenylmethylthio group.

An easily removable organic silyl or stannyl group can preferably carry, as substituents, optionally substituted, especially aliphatic hydrocarbon radicals, such as lower alkyl, for example methyl, ethyl or tert.-butyl, or halogeno-lower alkyl, for example 2-chloroethyl, and also functional groups, for example etherified or esterified hydroxyl groups, such as lower alkoxy, for example methoxy or ethoxy, or halogen, for example chlorine. Such silyl or stannyl radicals are, inter alia, tri-lower alkylsilyl, for example trimethylsilyl or tert.-butyldimethylsilyl, lower alkoxy-lower alkyl-halogeno-silyl, for example chloro-methoxy-methyl-silyl or tri-lower alkyl-stannyl, for example tri-n-butyl-stannyl.

An etherified hydroxyl or mercapto group $R_1$ is, for example, a $-O-R_3$ or $-S-R_3$ group, wherein $R_3$ represents a lower aliphatic hydrocarbon radical and above all denotes lower alkyl, especially methyl, or a $-S-R_4$ group, wherein $R_4$ represents the radical of an optionally substituted heterocyclic, monocyclic or bicyclic ring system which is bonded to the sulphur by a ring carbon atom and contains 1 to 4 nitrogen atoms and optionally a further ring hetero-atom from the group of oxygen and sulphur, or a $-S-R_5$ group, wherein $R_5$ denotes the radical of an optionally substituted heterocyclic, monocyclic or bicyclic ring system which is bonded to the sulphur by a ring carbon atom and contains a six-membered ring with one or two nitrogen atoms, with one nitrogen atom of this ring system carrying an oxido group or one carbon atom carrying an oxo group.

A lower alkyl group $R_3$ can be branched or unbranched and has, for example, up to 7, preferably up to 4, carbon atoms; such radicals are, for example, methyl, ethyl, n-propyl, isopropyl, n-butyl, isobutyl, sec.-butyl or tert.-butyl and also n-pentyl, isopentyl, n-hexyl, isohexyl or n-heptyl.

A group $R_4$ is, for example, a diazolyl, triazolyl, tetrazolyl, thiazolyl, thiadiazolyl, thiatriazolyl, oxazolyl, oxadiazolyl, benzimidazolyl, benzoxazolyl, triazolopyridyl or purinyl group which can optionally be substituted by halogen, for example fluorine, chlorine or bromine, amino, such as amino optionally substituted by lower alkyl, for example amino, methylamino or dimethylamino, nitro, lower alkyl, for example as mentioned above, cycloalkyl, for example cyclopentyl or cyclohexyl, lower alkoxy, for example methoxy or ethoxy, aryl, for example phenyl, or substituted phenyl, for example phenyl containing halogen, such as chlorine, or aralkyl, for example benzyl, furyl, thienyl or oxazolyl, it being possible for one or several such substituents to be present.

Preferred groups $R_4$ are imidazol-2-yl, 1-methyl-1H-1,2,3-triazol-4-yl, 1H-1,2,4-triazol-3-yl, 5-methyl-1H-1,2,4-triazol-3-yl, 3-methyl-1-phenyl-1H-1,2,4-triazol-5-yl, 4,5-dimethyl-4H-1,2,4-triazol-3-yl, 4-phenyl-4H-1,2,4-triazol-3-yl, 1H-tetrazol-5-yl, 1-methyl-1H-tetrazol-5-yl, 1-ethyl-1H-tetrazol-5-yl, 1-n-propyl-1H-tetrazol-5-yl, 1-phenyl-1H-tetrazol-5-yl, 1-p-chlorophenyl-1H-tetrazol-5-yl, 2-thiazolyl, 4-(2-thienyl)-2-thiazolyl, 4,5-dimethyl-2-thiazolyl, 1,3,4-thiadiazol-2-yl, 2-methyl-1,3,4-thiadiazol-5-yl, 2-ethyl-1,3,4-thiadiazol-5-yl, 2-n-propyl-1,3,4-thiadiazol-5-yl, 2-isopropyl-1,3,4-thiadiazol-5-yl, 5-thiatriazolyl, 5-oxazolyl, 4-methyl-5-oxazolyl, 2-oxazolyl, 4,5-diphenyl-2-oxazolyl, 3-methyl-5-isoxazolyl, 1,2,4-oxadiazol-5-yl, 2-methyl-1,3,4-oxadiazol-5-yl, 2-phenyl-1,3,4-oxadiazol-5-yl, 5-p-nitrophenyl-1,3,4-oxadiazol-2-yl, 2-(2-thienyl)-1,3,4oxadiazol-5-yl, 2-benzimidazolyl, 5-chloro-2-benzimidazolyl, 2-benzoxazolyl, 5-nitro-2-benzoxazolyl, 5-chloro-2-benzoxazolyl, s-triazolo[4,3-a]pyrid-3-yl, 3H-v-triazolo[4,5-b]pyrid-5yl, purin-2-yl, purin-6-yl and 8-chloro-2-methylpurin-6-yl.

A group $R_5$ is, for example a N-oxido-pyridyl, N-oxido-pyridazinyl or 2-oxo-pyrimidyl group, in which the heterocyclic six-membered ring can be substituted, for example for one or more halogen atoms, or by nitro, amino, mono- or di-lower alkylamino, lower alkyl, lower alkoxy, hydroxy-lower alkyl, such as hydroxymethyl, or carboxyl groups, and also an oxo-purinyl group.

Preferred groups $R_5$ are 1-oxido-2-pyridyl, 1-oxido-4-chloro-2-pyridyl, 2-oxido-6-pyridazinyl, 1-oxido-3-chloro-6-pyridazinyl, 1-oxido-6-methyl-3-pyridazinyl, 1-oxido-3-methoxy-6-pyridazinyl, 1-oxido-3-ethoxy-6-pyridazinyl, 1-oxido-3butoxy-6-pyridazinyl or 1-oxido-3-(2ethylhexyloxy)-6-pyridazinyl. Amongst the 2-oxo-pyrimidinyl groups the 2-oxo-4-pyrimidinyl, 6-methyl-2-oxo-4-pyrimidinyl, 5-methyl-2-oxo-4-pyrimidinyl, 6-amino-2-oxo-4-pyrimidinyl, 6-dimethylamino-2-oxo-4-pyrimidinyl, 5-carboxy-2oxo-4-pyrimidinyl or 6-carboxy-2oxo-4-pyrimidinyl group may be mentioned as examples. As an oxo-purinyl group, $R_5$ can be, for example, the 2-oxo-6-purinyl group.

An esterified hydroxyl group $R_1$ is, for example, a —O—$R_6$ group, wherein $R_6$ denotes lower alkanoyl with up to 7, preferably with up to 4, carbon atoms. Lower alkanoyl is, for example, formyl, propionyl, valeryl, hexanoyl, heptanoyl and especially acetyl.

An esterified mercapto group $R_1$ is, for example, a mercapto group esterified by benzoic acid, or a —S—$R_6$ group, wherein $R_6$ has the above meaning, or a —S—C(=O)—$R_4$ group, wherein $R_4$ has the above meaning and in particular represents 1-methyl-1,2,3-triazol-4-yl, 1,2,3-thiadiazol-4-yl, 1,2,3-thiadiazol-5-yl, 3-methylisoxazol-5-yl, 1,2,3-thiadiazol-5-yl, 1,2,5-thiadiazol-4-yl, 3-methyl-isoxazol-5-yl, 3-isothiazolyl, 4-isothiazolyl or 5-isothiazolyl.

An esterified hydroxyl group $R_1$ is furthermore a —O—$R_7$ group, wherein $R_7$ denotes a carbamoyl radical of the formula —CO—NH—$(CO)_n$—$R_8$, wherein $n$ can be 1 or, preferably, 0, and $R_8$ represents an unsubstituted or halogen-substituted lower alkyl radical with, preferably, up to 4 carbon atoms, and wherein the substituent, for example chlorine, is above all in the $\beta$- or $\gamma$-position or wherein $R_8$, if $n$ is 0, can also be hydrogen.

The carbamoyl, N-methylcarbamoyl, N-ethylcarbamoyl, N-(2-chloroethyl)carbamoyl and N-acetylcarbamoyl group are representative examples of such groups $R_7$.

A quaternary ammonium group $R_1$ is a group $R_9^+$ derived from a tertiary amine, wherein the nitrogen atom is bonded to the methyl carbon atom and accordingly is in the quaternised positively charged form. Quaternary ammonium groups $R_9^+$ are, for example, tri-lower alkylammonium, such as trimethylammonium, triethylammonium, tripropylammonium or tributylammonium, and, in particular, optionally substituted aromatic heterocyclic ammonium groups with 1 or 2 nitrogen atoms and optionally one sulphur atom, such as pyrimidinium, pyridazinium, thiazolium, quinolinium and above all pyridinium, which are monosubstituted or di-substituted, for example by lower alkyl, such as methyl, hydroxy-lower alkyl, such as hydroxymethyl, amino, sulphonamido, such as p-aminobenzenesulphonamido, hydroxyl, halogen, halogen-lower alkyl, such as trifluoromethyl, sulphonyl, carboxyl, lower alkoxycarbonyl, such as methoxycarbonyl, nitrile, carboxamido which is optionally N-mono-substituted or N,N-disubstituted by lower alkyl or hydroxy-lower alkyl, carboxy-lower alkyl, such as carboxymethyl, lower alkanoyl, such as acetyl, or N-lower alkylpyrrolidinyl, such as 2-N-methylpyrrolidinyl.

Examples of heterocyclic ammonium groups $R_9^+$ are pyridinium, 2-, 3- or 4-methyl-, 3,5-dimethyl-, 2,4,6-trimethyl-, 2-, 3- or 4-ethyl-, 2-, 3- or 4-propyl- or especially 4-hydroxymethyl-, 2-amino-, 2-amino-6-methyl-, 2-sulphanilamido-, 3-hydroxy-, 3-fluoro-, 3-chloro-, 3-iodo- or especially 3-bromo-, 4-trifluoromethyl-, 3-sulphonyl-, 2-, 3- or 4-carboxy-, 2,3-dicarboxy-, 4-methoxycarbonyl-, 3- or 4-cyano-, 3-carboxymethyl-, 3- or 4-acetyl, 3-(1-methyl-2-pyrrolidinyl)- and especially 4-carboxamido- and also 3-carboxamido-, 3- or 4-N-methylcarboxamido-, 4-N,N-dimethylcarboxamido-, 4-N-ethylcarboxamido-, 3-N,N-diethylcarboxamido, 4-N-propylcarboxamido-, 4-isopropylcarboxamido- and 4-hydroxymethylcarboxamido-pyridinium and also pyrimidinium, pyridazinium, thiazolium or quinolinium.

A protected carboxyl group of the formula —C(=O)—$R_2$ is above all an esterified carboxyl group which can preferably be split easily and wherein the carboxyl protective radical $R_2$ represents an etherified hydroxyl group.

An etherified hydroxyl group $R_2$ which forms, with the carbonyl grouping of the formula —C(=O)—, an esterified carboxyl group which can preferably be split easily is, for example, a lower alkoxy group which is preferably substituted, above all in the $\alpha$-position but also in the $\beta$-position and/or branched in the $\alpha$-position. Substituents of such a group are, for example, carbocyclic aryl, such as phenyl which is optionally substituted, for example by lower alkyl, such as tert.-butyl, phenyl, hydroxyl, lower alkoxy, such as methoxy, and/or nitro, furyl, such as 2-furyl, aryloxy, such as phenyloxy which is optionally substituted, for example by lower alkoxy, such as methoxy, arylcarbonyl, such as benzoyl which is optionally substituted, for example by halogen, such as bromine, nitrile or acylamino, such as diacylamino, for example phthalimino or succinylimino; such substituents are preferably in the $\alpha$-position of the lower alkoxy group $R_2$, and the latter can contain one or two, but also three, such radicals, depending on the nature of the substituents. Further substituents which are preferably in the β-position of the lower alkoxy radical $R_2$ are halogen, for example chlorine, bromine or iodine, and in such radicals it is easily possible, for example, to convert chlorine and bromine into iodine. Examples of the optionally substituted lower alkoxy groups $R_2$ which have been mentioned are tert.-lower alkoxy, for example tert.-butoxy or tert.-pentoxy, α-phenyl-lower alkoxy which is optionally substituted in the phenyl radical, for example as indicated, such as 4-hydroxy-3,5-di-tert.-butyl-benzyloxy, 2-biphenylyl-2-propoxy, 4-methoxy-benzyloxy, 4,5-dimethoxy-2-nitrobenzyloxy or 4-nitro-benzyloxy, diphenylmethoxy which is optionally substituted in the phenyl radicals, for example as indicated, especially by lower alkoxy, such as benzhydryloxy or 4,4'-dimethoxy-diphenylmethoxy, trityloxy, bis-phenyloxymethoxy which is optionally substituted in the phenyl radicals, for example as indicated, especially by lower alkoxy, such as bis-4-methoxyphenyloxy-methoxy, 2-halogeno-lower alkoxy, such as 2,2,2-trichloroethoxy, 2-bromoethoxy or 2-iodoethoxy, phenacyloxy which is optionally substituted, especially by halogen, such as phenacyloxy or 4-bromophenacyloxy, cyanomethoxy or diacyliminomethoxy, such as phthalyliminomethoxy or succinyliminomethoxy.

Further, an etherified hydroxyl group $R_2$, which forms, with the carbonyl grouping of the formula —C(=O)—, an esterified carboxyl group which can be split, preferably easily, also denotes a cycloalkoxy group of which the α-position preferably represents a bridgehead carbon atom. An example of such a cycloalkoxy group $R_2$ is 1-adamantyloxy.

Further radicals $R_2$ are organic silyloxy or stannyloxy groups which contain 1 to 3 organic radicals, especially optionally substituted aliphatic hydrocarbon radicals, such as lower alkyl, for example methyl, ethyl, n-propyl or tert.-butyl, or halogeno-lower alkyl, for example chloromethyl or 2-chloroethyl, and also optionally substituted cycloaliphatic, aromatic or araliphatic hydrocarbon radicals, such as cycloalkyl, phenyl or phenyl-lower alkyl, as well as organic-substituted functional groups, such as etherfied hydroxyl groups, for example lower alkoxy, such as methoxy or ethoxy, and which can optionally contain, for example, halogen, such as chlorine, as further substituents. Such radicals $R_2$ are, inter alia, tri-lower alkylsilyloxy, such as trimethylsilyloxy, tert.-butyldimethylsilyloxy, lower alkoxy-lower alkyl-halogeno-silyloxy, for example chloromethoxy-methyl-silyloxy or tri-lower alkylstannyloxy, for example tri-n-butylstannyloxy.

The group $R_2$ can also represent a phosphoryloxy group which contains a substituted trivalent or pentavalent phosphorus atom and which, together with the carbonyl grouping of the formula —C(=O)—, forms a protected carboxyl group. Substituents of trivalent phosphorus are, inter alia, optionally substituted hydrocarbon radicals, such as appropriate aliphatic or araliphatic hydrocarbon radicals, for example lower alkyl or halogeno-lower alkyl, such as methyl, ethyl or chloromethyl, or phenyl-lower alkyl, such as benzyl, etherified hydroxyl or mercapto groups, such as hydroxyl or mercapto groups etherified by optionally substituted aliphatic, aromatic or araliphatic hydrocarbon radicals, for example lower alkoxy or lower alkylthio, such as methoxy, ethoxy, methylthio or n-butylthio, phenyloxy or phenylthio, which is optionally substituted, for example by lower alkyl, lower alkoxy or halogen, or phenyl-lower alkoxy or phenyl-lower alkylthio which are optionally substituted, for example by lower alkyl, lower alkoxy or halogen, for example benzyloxy or benzylthio, halogen, for example fluorine, chlorine or bromine, or a bivalent hydrocarbon radical which is optionally substituted and/or interrupted by heteroatoms, such as oxygen or sulphur, such as an appropriate aliphatic or araliphatic radical, for example lower alkylene, such as 1,4-butylene or 1,5-pentylene, or 1-oxa-lower alkylene, for example 1-oxa-1,4-pentylene or 1-oxa-1,5-pentylene, or two hydroxyl groups etherified by a bivalent optionally substituted hydrocarbon radical, such as an appropriate aliphatic, aromatic or araliphatic radical, such as lower alkylene or 1,2-phenylene. Substituents of pentavalent phosphorus are those of trivalent phosphorus and, additionally, an oxo group.

The esterified carboxyl groups of the formula —C(=O)—$R_2$ which can be split under physiological conditions should be singled out particularly. In such a group, $R_2$ is above all an acyloxymethoxy group, wherein acyl denotes, for example, the radical of an organic carboxylic acid, above all of an optionally substituted lower alkanecarboxylic acid, or wherein acyloxymethyl forms the radical of a lactone. Such groups $R_2$ are lower alkanoyloxymethoxy, for example acetoxymethoxy or pivaloyloxymethoxy, amino-lower alkanoyloxymethoxy, especially α-amino-lower alkanoyloxymethoxy, for example glycyloxymethoxy, L-valyloxymethoxy or L-leucycloxymethoxy, and also phthalidyloxy.

Salts are, in particular, salts of compounds of the formula I having a free carboxyl group —C(=O)—$R_2$, above all metal salts or ammonium salts, such as alkali metal salts and alkaline earth metal salts, for example sodium salts, potassium salts, magnesium salts or calcium salts, and also ammonium salts with ammonia or suitable organic amines, it being possible, above all, to use aliphatic, cycloaliphatic, cycloaliphatic-aliphatic and araliphatic primary, secondary or tertiary monoamines, diamines or polyamines, as well as heterocyclic bases, for forming the salts, such as lower alkylamines, for example triethylamine, hydroxy-lower alkylamines, for example 2-hydroxyethylamine, bis-(2-hydroxyethyl)-amine or tris-(2-hydroxyethyl)-amine, basic aliphatic esters of carboxylic acids, for example 4-aminobenzoic acid 2-diethylaminoethyl ester, lower alkyleneamines, for example 1-ethylpiperidine, cycloalkylamines, for example dicyclohexylamine, or benzylamines, for example N,N'-dibenzylethylenediamine, and also bases of the pyridine type, for example pyridine, collidine or quinoline. Compounds of the formula I can also form acid addition salts, for example with inorganic acids, such as hydrochloric acid, sulphuric acid or phosphoric acid, or with suitable organic carboxylic acids, or sulphonic acids, for example trifluoroacetic acid. Compounds of the formula I with an acid group and a basic group can also be in the form of inner salts, that is to say in the form of zwitter-ions.

Compounds of the formula I, wherein X and $R_1$ have the above meanings, R denotes hydrogen and $R_2$ represents hydroxyl or a radical which, together with the carbonyl grouping of the formula —C(=O)—, forms an esterified carboxyl group which can be split under physiological conditions, and their physiologically acceptable salts, are valuable antibiotically active substances which can, in particular, be used as antibacterial antibiotics. For example, they are active against micro-organisms, such as Gram-positive bacteria, for example Staphylococcus aureus (for example in mice in doses of about 2 to 5 mg/kg given subcutaneously) and Gram-negative bacteria, for example *Escherichia coli* (β-lactamase-negative) (for example in mice, in doses of about 20 to 70 mg/kg given subcutaneously) or *Escherichia coli* (β-lactamase-positive) (for example in mice in doses of about 60 mg/kg given subcutaneously). The antibacterial action in vitro can be demonstrated in a range down to about 0.03 γ/ml. These new compounds can therefore be used accordingly, for example in the form of antibiotically active preparations.

Compounds of the formula I, wherein X, $R_1$ and $R_2$ have the above meanings and R represents an amino protective group, as well as their salts, are valuable intermediate products, which are usefull for the preparation of compounds of the formula I wherein R is hydrogen or of derivatives of the compounds of formula I wherein the 7β-position is substituted by lower alkoxy as described in application Ser. No. 505,887.

The present invention above all relates to those compounds of the formula I, wherein X represents oxygen or, in particular, sulphur, R denotes an amino protective group or especially hydrogen, $R_1$ represents hydrogen, hydroxy, lower alkanoyloxy, especially acetoxy, or a radical of the formula $—S—R_4$, $—S—R_5$ or $—R_9^+$, and $R_2$ represents a carboxyl protective radical which together with the carbonyl grouping of the formula $—C(=O)—$ forms a protected carboxyl group, or in particular represents hydroxyl, and also salts, especially the non-toxic, pharmaceutically usable salts, especially the alkali metal salts or alkaline earth metal salts, the acid addition salts with hydrochloric or sulfuric acid, as well as the inner salts, of such compounds.

In particular, the present invention relates to ceph-3-em compounds of the formula I, wherein X represents oxygen or especially sulphur, R denotes an amino protective group or especially hydrogen, $R_1$ represents hydrogen, hydroxy, lower alkanoyloxy, especially acetoxy, or represents the radical of the formula $—S—R_4$, in which $R_4$ represents a monocyclic, five-membered heterocyclic radical of aromatic character which is bonded to the sulphur atom by a carbon atom and contains 2 to 4 ring nitrogen atoms and optionally a ring oxygen atom or ring sulphur atom and which can optionally be substituted by lower alkyl, especially methyl, or represents a radical of the formula $—S—R_5$, wherein $R_5$ represents an unsaturated monocyclic six-membered heterocyclic radical which is bonded to the sulphur atom by a carbon atom and contains 2 ring nitrogen atoms, with either one ring nitrogen atom containing an oxido group or one ring carbon atom containing an oxo group, and which can optionally be substituted by lower alkyl, for example methyl, lower alkoxy, for example methoxy or halogen, for example chlorine, or represents a radical $—R_9^+$, which denotes a pyridinium radical which can optionally be substituted by halogen, for example chlorine or bromine, lower alkyl, for example 4-methyl or 4-ethyl, carboxyl, carbamoyl or hydrazinocarbonyl, and wherein $R_2$ represents a carboxyl protective radical which together with the carbonyl grouping of the formula $—C(=O)—$ forms a protected carboxyl group or in particular represents hydroxyl, and also salts, for example the non-toxic pharmaceutically usable salts, especially the alkali metal salts or alkaline earth metal salts, the acid addition salts with hydrochloric or sulfuric acid, as well as the inner salts, of such compounds.

Preferred ceph-3-em compounds of the formula I are those wherein X represents oxygen or especially sulphur, R denotes an amino protective group or especially hydrogen, $R_1$ denotes hydrogen, hydroxy, lower alkanoyloxy, especially acetoxy or denotes a group of the formula $—S—R_4$, wherein $R_4$ represents a thiadiazolyl radical which is optionally substituted by lower alkyl, for example methyl and is bonded to the sulphur atom by a ring carbon atom, for example 5-methyl-1,3,4-thiadiazol-2-yl or 5-methyl-1,2,4-thiadiazol-3-yl, or a similarly substituted and bonded tetrazolyl radical, for example 1-methyl-5-tetrazolyl, or denotes a group of the formula $—S—R_5$, wherein $R_5$ represents a N-oxido-pyridazinyl radical which is optionally substituted by lower alkyl, for example methyl, lower alkoxy, for example methoxy or halogen, for example chlorine and is bonded to the sulphur atom by a ring carbon atom, for example 6-methyl-1-oxido-3-pyridazinyl, 6-methoxy-1-oxido-3-pyridazinyl or 6-chloro-1-oxido-3-pyridazinyl, or denotes a group of the formula $—R_9^+$, which represents a pyridinium radical which is optionally substituted by carbamoyl, for example pyridinium or 3-carbamoyl-pyridinium, and wherein $R_2$ represents a carboxyl protective radical which together with the carbonyl grouping of the formula $—C(=O)—$ forms a protected carboxyl group, or in particular represents hydroxyl, as well as salts, for example the non-toxic pharmaceutically usable salts, especially the alkali metal salts or alkaline earth metal salts, the acid addition salts with hydrochloric or sulfuric acid, as well as the inner salts, of such compounds.

Primarily the present invention relates to compounds of the formula I wherein X is oxygen or especially sulphur, R denotes hydrogen, lower alkoxycarbonyl, which preferably on the carbon atom in the α-position to the oxy group carries several aliphatic substituents or is branched, or a methoxycarbonyl group which is substituted by an arylcarbonyl radical, especially by a benzoyl radical, or a lower alkoxycarbonyl group which is substituted by halogen in the β-position, such as tert.-butoxycarbonyl, tert.-pentoxycarbonyl, phenacyloxycarbonyl, 2,2,2-trichloroethoxycarbonyl or 2-iodoethoxycarbonyl or phenyl-lower alkoxycarbonyl which is optionally substituted, for example, by lower alkyl, hydroxy, lower alkoxy or nitro, especially α-phenyl-lower alkoxycarbonyl, for example benzyloxy- or 4-nitrobenzyloxycarbonyl, and also diphenylmethoxycarbonyl which is optionally substituted for example by lower alkoxy, for example 4,4'-dimethoxy-diphenylmethoxycarbonyl, or R denotes an arylmethyl or polyarylmethyl group which is optionally substituted by lower alkoxy, especially by o- and/or p-methoxy, such as benzyl, p-methoxybenzyl or trityl, $R_1$ denotes hydrogen, hydroxy, lower alkanoyloxy with up to 4 carbon atoms, especially acetoxy, a radical $—S—R_4$ wherein $R_4$ is tetrazolyl or thiadiazolyl substituted by lower alkyl, especially 1-methyl-1H-tetrazol-5-yl and 5-methyl-1,3,4-thiadiazol-2-yl, or a radical $—S—R_5$, wherein $R_5$ is N-oxido-pyridazinyl substituted by lower alkyl, especially 6-methyl-1-oxido-pyridazin-3-yl, or $R_1$ is a pyridinium group, and $R_2$ is hydroxy, tri-lower alkyl silyloxy, especially trimethylsilyloxy or lower alkoxy, which is preferably branched at the α-position or is substituted in the α-position by unsubstituted or by lower alkoxy or nitro substituted phenyl, or by benzoyl, or which is substituted in the β-position by halogen, especially tert.-butoxy, benzyloxy, 4-nitrobenzyloxy, diphenylmethoxy, 4,4'-dimethoxy-diphenylmethoxy, phenacyl, 2,2,2-trichloroethoxy or 2-iodoethoxy, as well as salts, for example the non-toxic pharmaceutically usable salts, especially the alkali metal salts or alkaline earth metal salts, the acid addition salts, especially with hydrochlorid or sulfuric acid, and the inner salts, of such compounds.

The new compounds of the present invention can be manufactured in a manner which is in itself known by acylating the amino group in a compound of the formula

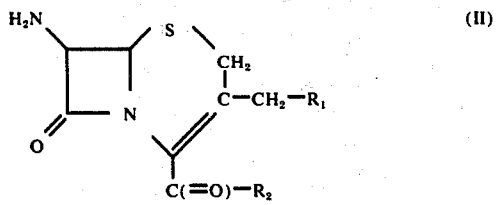

wherein the amino group is optionally substituted by a group which permits acylation to take place, and wherein $R_1$ and $R_2$ have the abovementioned meanings, or in a salt thereof, by treatment with an acid of the formula

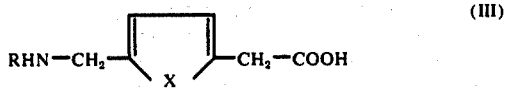

wherein X and R have the abovementioned meanings, or with a reactive functional acid derivative thereof and, if desired or required, in a resulting compound converting a protected amino group in the aminomethyl radical into the free amino group and/or converting a protected carboxyl group of the formula $-C(=O)-R_2$ into a free carboxyl group or a carboxyl group which is protected in a different way, and/or converting a group $R_1$ into another group $R_1$ and/or, if desired, converting a resulting salt into the free compound or into another salt or converting a resulting free compound into a salt.

The groups which permit acylation to take place and which are optionally present on the amino group of a starting material of the formula II are, for example, organic silyl or stannyl groups and also ylidene groups which together with the amino group form a Schiff's base. The said organic silyl or stannyl groups are the same as those which are also capable of forming the protected carboxyl group $-C(=O)-R_2$ with the carboxyl group on the cephem ring. When silylating or stannylating the carboxyl group, the amino group can be silylated or stannylated simultaneously if an excess of the silylating or stannylating agent is used.

The ylidene groups mentioned are in particular arylmethylene groups, wherein aryl in particular represents a carbocyclic, above all monocyclic, aryl radical, for example phenyl optionally substituted by nitro or hydroxyl, such arylmethylene groups are, for example, benzylidene, 2-hydroxybenzylidene or 4-nitrobenzylidene.

In a starting material of the formula II, further free functional groups which may be present in addition to the carboxyl group, such as a free hydroxyl group $R_1$, are usually present during the acylation reaction in a protected form, if desired a protected form which can be split easily; for example, a free hydroxyl group can be in an etherified or esterified form which can be split easily.

The starting material of the formula III can also be used in the form of an acid addition salt in which the amino group is in the protonised ionic form.

The acylation of the free amino group or of the amino group which is substituted by a group which permits the acylation to take place, in the starting material of the formula II, can be effected in a known manner by treatment with an acid of the formula III or a reactive functional derivative thereof.

If a free acid of the formula III, preferably with a protected amino group, is employed for the acylation, suitable condensation agents are usually employed, such as carbodiimides, for example N,N'-diethyl-, N,N'-dipropyl-, N,N'-diisopropyl-, N,N'-dicyclohexyl or N-ethyl-N'-γ-dimethylaminopropyl-carbodiimide, suitable carbonyl compounds, for example carbonyldiimidazole, or isoxazolinium salts, for example N-ethyl-5-phenyl-isoxazolinium-3'-sulphonate and N-tert.-butyl-5-methyl-isoxazolinium perchlorate, or an acylamino compound, for example 2-ethoxy-1-ethoxycarbonyl-1,2-dihydroquinoline.

The condensation reaction is preferably carried out in one of the anhydrous reaction media mentioned below, for example in methylene chloride, dimethylformamide or acetonitrile.

An amide-forming, functional derivative of an acid of the formula III, preferably with a protected amino group, is above all an anhydride of such an acid, including a mixed anhydride, but also an inner anhydride. Mixed anhydrides are, for example, those with inorganic acids, such as hydrogen halide acids, that is to say the corresponding acid halides, for example chlorides or bromides, and also those with an acid containing phosphorus, for example phosphoric acid or phosphorous acid, or with an acid containing sulphur, for example sulphuric acid. Further mixed anhydrides are, for example, those with organic carboxylic acids, such as with lower alkanecarboxylic acids which are optionally substituted, for example, by halogen, such as fluorine or chlorine, for example pivalic acid or trichloroacetic acid, or with lower alkyl half-esters of carbonic acid, such as the ethyl or isobutyl half-ester of carbonic acid, or with organic, especially aliphatic or aromatic, sulphonic acids, for example p-toluenesulphonic acid.

Further acid derivatives of an acid of the formula III which are suitable for reaction with the free amino group are activated esters, usually with a protected amino group in the aminomethyl grouping, such as phenyl esters which are preferably substituted, for example by nitro or halogen, such as chlorine, for example pentachlorophenyl or 4-nitrophenyl esters or 2,4-dinitrophenyl esters, or hetero-aromatic esters, such as benztriazole esters, for example 2-benztriazole esters, or diacylimino esters, such as succinylimino esters or phthalylimino esters, and also the azide of the acid of the formula III, wherein the amino group is preferably protected.

The acylation with an acid derivative, such an an anhydride, and especially with an acid halide, can be carried out in the presence of an acid-binding agent, for example an organic base, such as an organic amine, for example a tertiary amine, such as a tri-lower alkylamine, for example such as triethylamine, or N,N-di-lower alkyl-aniline, for example N,N-dimethylaniline, an inorganic base, for example an alkali metal or alkaline earth metal hydroxide, carbonate or bicarbonate, for example sodium, potassium or calcium hydroxide, carbonate or bicarbonate, or an oxirane, for example a lower 1,2-alkylene oxide, such as ethylene oxide or propylene oxide.

The above acylation can be carried out in an aqueous or preferably in a non-aqueous solvent or solvent mixture, for example in a carboxylic acid amide, such as a N,N-di-lower alkylamide, for example dimethylformamide, a halogenated hydrocarbon, for example methylene chloride carbon tetrachloride or chlorobenzene, a ketone, for example acetone, an ester, for example ethyl acetate, or a nitrile, for example acetonitrile, or mixtures thereof, and, if necessary, at lowered or raised temperature and/or in an inert gas atmosphere, for example a nitrogen atmosphere.

In an acid of the formula III or in an acid derivative thereof, the amino group is preferably in the protected form, and an acid derivative can, if desired, be formed in situ. Thus, for example, a mixed anhydride is obtained by treating an acid of the formula III or a suitable salt thereof, such as an ammonium salt, for example with an organic amine, such as N-methylmorpholine, or a metal salt, with a suitable acid derivative, such as a corresponding acid halide of an optionally substituted lower alkanecarboxylic acid, for example trichloroacetyl chloride, or with a half-ester of a carbonic acid half-halide, for example chloroformic acid ethyl ester or isobutyl ester, and the mixed anhydride thus obtainable is used without isolation.

In a resulting compound functional groups can, if desired or required, be converted into other functional groups in a manner which is in itself known. Above all it is possible, in a compound obtainable according to the invention, to liberate a protected amino group RHN— in the aminomethyl substituent of the acylamino group and/or to convert a protected carboxyl grouping of the formula —C(=O)—$R_2$ into a free carboxyl group; furthermore, a free carboxyl group of the formula —C(=O)—$R_2$ can be converted in a manner which is in itself known into a protected carboxyl group, especially a physiologically splittable esterified carboxyl group, of the formula —C(=O)—$R_2$ and/or a group $R_1$ can be converted into another group $R_1$. These conversions are carried out in a manner which is in itself known, the sequence, in the case of multiple conversions, being optional and usually depending on the nature of the radicals to be converted or to be split off and on the reactions used for the purpose. Furthermore it is possible simultaneously to convert more than one protected functional group into the corresponding free functional groups. Thus it is possible, for example by treatment with a suitable acid, such as trifluoroacetic acid, optionally in the presence of anisole, simultaneously to convert, in a resulting compound, a tert.-butoxycarbonylamino or diphenylmethoxycarbonylamino group in the aminomethyl substituent of the acylamino radical in the 7-position, and a diphenylmethoxycarbonyl group representing the radical of the formula —C(=O)—$R_2$, into the amino and carboxyl group respectively.

The conversion of a protected amino group into a free amino group can be effected in a manner which is in itself known, by solvolysis or reduction.

A formyl group as the amino protective group can be split off, for example, by treatment with an acid agent, for example p-toluenesulphonic acid or hydrochloric acid, with a weakly basic agent, for example dilute ammonia, or with a decarbonylating agent, for example tris-(triphenylphosphine)-rhodium chloride.

In a resulting compound, it is possible to remove, from an acylamino group, an easily removable acyl group such as an α-poly-branched lower alkoxycarbonyl group, for example tert.-butoxycarbonyl, or a polycyclic cycloalkoxycarbonyl group, for example 1-adamantyloxycarbonyl, an optionally substituted diphenylmethoxycarbonyl group, for example diphenylmethoxycarbonyl, or an α-furyl-lower alkoxycarbonyl group, and also a 4-hydroxy-3,5-bis-tert.-butyl-benzyloxycarbonyl group, for example by treatment with a suitable acid, such as formic acid or trifluoroacetic acid, optionally in the presence of anisole, and a 2-halogeno-lower alkoxycarbonyl group, such as 2,2,2-trichloroethoxycarbonyl or 2-iodoethoxycarbonyl, or a phenacyloxycarbonyl group, by treatment with a suitable reducing agent or an appropriate metal compound, for example zinc, or a chromium-II compound, such as chromium-II chloride or acetate, usually in the presence of an agent which together with the metal or the metal compound generates nascent hydrogen, preferably in the presence of aqueous acetic acid. A phenacyloxycarbonyl group can also be split off by treatment with a suitable nucleophilic, preferably salt-forming, reagent, such as sodium thiophenolate.

It is furthermore possible, in a resulting compound, to split an amino group protected by a suitably substituted benzyloxycarbonyl group, such as 4-methoxybenzyloxycarbonylamino or 4-nitrobenzyloxycarbonylamino, hydrogenolytically, for example by treatment with hydrogen in the presence of a hydrogenation catalyst, for example palladium.

A triarylmethyl group, such as the trityl group, can, for example, be split off by treatment with an acid agent, such as a mineral acid, for example hydrochloric acid.

An amino group protected in the form of an enamine or of a ketimine tautomeric therewith, and the said amino groups protected by arylthio, aralkylthio and arylsulphonyl can be split, for example, by treatment with an acid agent, above all an aqueous acid, such as an organic carboxylic acid, for example formic acid, acetic acid or propionic acid, or a mineral acid, for example hydrochloric acid or sulphuric acid, optionally in the presence of a water-miscible solvent, such as a lower alkanol, for example methanol, a ketone, for example acetone, an ether, for example tetrahydrofurane, or a nitrile, for example acetonitrile. The splitting off of the thio protective groups mentioned can be effected particularly rapidly in the presence of additional reagents, such as sodium thiosulphate, sulphurous acid, thioacetamide, thiourea and potassium iodide.

An amino group, protected with an organic silyl or stannyl group, in a resulting compound can be liberated by treatment with an aqueous or alcoholic agent, for example with a lower alkanol, such as methanol, or a mixture thereof; the splitting of an amino group protected in this way usually occurs already during working up of the acylation product.

The reaction products which are obtained in the acylation, according to the invention, of compounds of the formula II, wherein the amino group is substituted by a silyl or stannyl group, and which still contain the organic silyl or stannyl group on the amide nitrogen, are usually converted into compounds of the formula I during working up, especially under hydrolytic and/or alcoholytic conditions, for example such as are customary in splitting off organic silyl or stannyl groups from amino groups.

The reaction products which are produced in the acylation, according to the invention, of compounds of the formula II, wherein the amino group is substituted by an ylidene group, and wherein the ylidene group is present on the amino nitrogen, are also usually converted into compounds of the formula I during working up, especially by hydrolysis, for example by treatment with water.

In a compound of the formula I, obtainable according to the invention, which has a protected, especially an esterified, carboxyl group of the formula —(C=O)—$R_2$, this group can be converted to the free carboxyl group in a manner which is in itself known, by solvolysis or reduction, for example depending on the nature of the group $R_2$. An esterified carboxyl group, for example a carboxyl group esterified by a lower alkyl radical, such as methyl or ethyl, can be converted into a free carboxyl group by hydrolysis in a weakly basic medium, for example by treatment with an aqueous solution of an alkali metal hydroxide or carbonate or alkaline earth metal hydroxide or carbonate, for example sodium hydroxide or potassium hydroxide, preferably at a pH value of about 9 to 10 and optionally in the presence of a lower alkanol. A carboxyl group which is esterified by a suitable 2-halogeno-lower alkyl group, such as a 2,2,2-trichloroethyl group or a 2-iodoethyl group, or by an arylcarbonylmethyl group, such as phenacyl group, can be converted into the free carboxyl group by, for example, treatment with a chemical reducing agent, such as a metal, for example zinc, or a reducing metal salt, such as a chromium-II salt, for example chromium-II chloride, usually in the presence of a hydrogen donor which together with the metal can generate nascent hydrogen, such as an acid, above all acetic acid as well as formic acid, or an alcohol, water preferably being added, whilst a carboxyl group esterified by an arylcarbonyl group, for example a phenacyl group, can also be converted into the free carboxyl group by treatment with a nucleophilic, preferably salt-forming, reagent, such as sodium thiophenolate or sodium iodide. A carboxyl group esterified by a suitable arylmethyl group can be converted into the free carboxyl group by, for example, irradiation, preferably with ultraviolet light, for example below 290 m$\mu$, if the arylmethyl group represents, for example, a benzyl radical which is optionally substituted in the 3-, 4- and/or 5-position, for example by lower alkoxy and/or nitro groups, or with ultraviolet light of longer wavelengths, for example above 290 m$\mu$, if the arylmethyl group denotes, for example a benzyl radical which is substituted by a nitro group in the 2-position.

The carboxyl group can be liberated from a carboxyl group esterified by a suitably branched lower alkyl group, for example tert.-butyl, by a suitable cycloalkyl group, such as 1-adamantyl, or a diphenylmethyl group, for example benzhydryl, for example by treatment with a suitable acid agent, such as formic acid or trifluoroacetic acid, optionally with addition of a nucleophilic compound, such as phenol or anisole. An acitvated esterified carboxyl group, such as a carboxyl group esterified by a suitably substituted phenyl radical or a diacylimino radical, as well as a carboxyl group esterified with the 4-hydroxy-3,5-di-tert.-butyl-benzyl radical, and also a carboxyl group present in the anhydride form, can be split by hydrolysis, in accordance with the nature of the ester or anhydride, for example by treatment with an acid or weakly basic aqueous agent, such as hydrochloric acid or aqueous sodium bicarbonate solution or an aqueous potassium phosphate buffer of pH about 7 to about 9, and an esterified carboxyl group which can be split hydrogenolytically, for example a carboxyl group esterified by 4-methoxybenzyl or 4-nitrobenzyl, can split by hydrogenolysis, for example by treatment with nascent hydrogen or with hydrogen in the presence of a noble metal catalyst, for example a palladium catalyst.

A carboxyl group protected, for example, by silylation or stannylation can be liberated in the usual manner, for example by treatment with water or an alcohol.

In a compound of the formula I obtainable in accordance with the process, which contains a free carboxyl group of the formula —C(=O)—$R_2$ and in which the amino group is optionally protected, the free carboxyl group can be converted in a manner which is in itself known into an esterified carboxyl group which can be split under physiological conditions. Thus, for example, a free carboxyl compound or a salt thereof, for example an alkali metal salt, such as the sodium salt or potassium salt, or an alkaline earth metal salt, such as a calcium salt or magnesium salt, or an optionally substituted ammonium salt, such as the triethylammonium salt, can be converted into the corresponding lower alkanoyloxymethoxycarbonyl group by reaction with a lower alkanoyloxymethyl halide, for example alkanoyloxymethyl chloride or bromide.

Furthermore, it is possible, in a compound of the formula I obtainable according to the invention, wherein the amino group in the aminomethyl substituent of the acylamino ester is preferably protected, to replace the group $R_1$ by another radical $R_1$, or convert it to another radical $R_1$, in a manner which is in itself known. Thus it is possible, for example, in a compound of the formula I, wherein $R_1$ represents, for example, a radical Y which is replaceable by nucleophilic substituents, or in a salt thereof, to replace such a radical Y by the —S—$R_3$, —S—$R_4$ or —S—$R_5$ group by treatment with a mercaptan compound of the formula HS—$R_3$, HS—$R_4$ or HS—$R_5$. A suitable radical Y is, for example, a free or esterified hydroxyl group, for example a hydroxyl group esterified by a hydrogen halide acid, such as hydrochloric acid or hydrobromic acid, or preferably by an organic carboxylic acid, such as an aliphatic carboxylic acid (including formic acid) or a cycloaliphatic, cycloaliphatic-aliphatic, aromatic, araliphatic, heterocyclic or heterocyclic-aliphatic carboxylic acid, or by a carbonic acid half-derivative, such as carbonic acid half-ester. Such esterified hydroxyl groups are, for example, optionally substituted lower alkanoyloxy, especially acetoxy, and also halogeno-lower alkanoyloxy, such as halogenoacetoxy, for example trifluoroacetoxy, as well as dichloroacetoxy, and also formyloxy, or optionally substituted benzoyloxy, such as 4-chlorobenzoyloxy.

The reaction of such a compound with a mercaptan of the formula HS—$R_3$, HS—$R_4$ or HS—$R_5$ can be carried out under neutral or weakly basic conditions in the presence of water and optionally of a water-miscible organic solvent. The basic conditions can be obtained, for example, by addition of an alkali metal hydroxide, carbonate or bicarbonate or alkaline earth metal hydroxide, carbonate or bicarbonate, for example sodium, potassium or calcium hydroxide, carbonate or bicarbonate. Examples of organic solvents which can be used are water-miscible alcohols, such as methanol or ethanol, ketones, such as acetone, amides, such as dimethylformamide, and the like.

It is furthermore possible to react a compound of the formula I, wherein $R_1$ represents, for example, the radical Y defined above and replaceable by nucleophilic substituents, with a tertiary amine $R_9$ under neutral or weakly acid conditions, preferably at a pH value of about 6.5, in the presence of water and optionally of a water-miscible organic solvent. The weakly acid conditions can be obtained by addition of a suitable organic or inorganic acid, for example acetic acid, hydrochloric acid, phosphoric acid or sulphuric acid. Examples of organic solvents which can be used are the water-miscible solvents mentioned above. To increase the yield, certain salts can be added to the reaction mixture, for example alkali metal salts such as sodium salts and especially potassium salts, of inorganic acids, such as hydrogen halide acids, for example hydrochloric acid and especially hydriodic acid as well as thiocyanic acid, or of organic acids, such as lower alkanecarboxylic acids, for example acetic acid. Examples of such salts are potassium iodide and potassium thiocyanate. Salts of suitable anion exchangers, for example of Amberlite LA-1, with acids, for example acetic acid, can also be used for this purpose.

Salts of compounds of the formula I can be prepared in a manner which is in itself known. Thus, salts of compounds of the formula I possessing acid groups can be formed, for example, by treatment with metal compounds, such as alkali metal salts of suitable carboxylic acids, for example the sodium salt of α-ethyl-caproic acid, or with ammonia or a suitable organic amine, preferably using stoichiometric amounts or only a slight excess of the salt-forming agent. Acid addition salts of compounds of the formula I which contain basic groupings are obtained in the usual manner, for example by treatment with an acid or with a suitable anion exchange reagent. Inner salts of compounds of the formula I which contain a free carboxyl group can be formed, for example, be neutralising salts, such as acid addition salts, to the isoelectric point, for example with weak bases, or by treatment with liquid ion exchangers.

Salts can be converted into the free compounds in the usual manner, metal salts and ammonium salts, for example, by treatment with suitable acids, and acid addition salts, for example, by treatment with a suitable basic agent.

The process also embraces those embodiments according to which compounds arising as intermediate products are used as starting materials and the remaining process steps are carried out with these, or the process is discontinued at any stage; furthermore, starting materials can be used in the form of derivatives or formed during the reaction.

preferably, those starting materials are used, and the reaction conditions are so chosen, that the compounds mentioned above as being particularly preferred are obtained.

Starting compounds of the formula II wherein the amino group is optionally substituted by a group which permits the acylation to take place are known or can be manufactured according to known methods.

Starting materials of the formula III can be manufactured according to methods which are in themselves known. For example, a compound of the formula IV

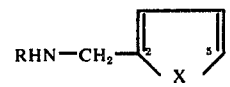

wherein X and R have the abovementioned meaning, or an acid addition salt thereof, such as the hydrochloride, can be acetylated in the 5-position, for example by treatment with a suitable acetylating agent, for example an acetic anhydride, including an acetyl halide, such as acetyl chloride, or preferably with acetic anhydride, in the presence of a suitable catalyst, such as a Lewis acid, for example aluminum chloride or aluminium bromide, or of an acid, such as polyphosphoric acid, or preferably trifluoroacetic acid as well as its anhydride, a 5-acetyl compound of the formula

being obtained. The reaction can be carried out in an anhydrous solvent, such as an optionally chlorinated hydrocarbon, for example 1,2-dichloroethane, or an excess of the liquid reagents employed, for example an excess of trifluoroacetic acid or acetic acid and/or their anhydrides. If trifluoroacetic acid or trifluoroacetic anhydride are used, a free amino group can at the same time be acylated by the trifluoroacetyl radical.

Compounds of the formula (V) can also be manufactured by reacting thiophene or furane with a N-(hydroxymethyl)-acylamide, for example with a N-(hydroxymethyl)-lower alkanoylamide, such as N-(hydroxymethyl)-trifluoroacetamide in the presence of a dehydrating agent, such as an organic or inorganic acid or a Lewis acid, for example trifluoroacetic acid, concentrated sulphuric acid, phosphorus pentoxide, polyphosphoric acid or aluminium chloride, optionally in an anhydrous solvent, such as glacial acetic acid, to give a 2-(acylaminomethyl)-thiophene or 2-(acylaminomethyl)-furane falling under the formula IV, and either isolating this compound or preferably acetylating it in the 5-position in the same reaction mixture by means of a suitable acetylating agent, such as acetic anhydride.

A 5-acetyl compound of the formula V, wherein the amino group is preferably protected, for example by the trifluoroacetyl radical, can for example be converted into a compound of the formula (III) by the method of Willgerodt or Willgerodt-Kindler, for example by heating with ammonium polysulphide or with a primary or secondary amine, such as morpholine, and subsequent hydrolysis of the thioamide formed as an intermediate.

Alternatively and preferably, a compound of the formula V, especially a compound wherein the amino group is protected, for example by the trifluoroacetyl radical, can be converted by warming with thallium-(III) nitrate in a lower alkanol, especially methanol, in the presence of an acid, for example perchloric acid, into a lower alkyl ester, for example the methyl ester, of an acid of the formula III, from which the free acid can be prepared by hydrolysis.

During the hydrolysis of a thioamide obtained by the Willgerodt or Willgerodt-Kindler method, or of an ester obtained by the thallium(III) nitrate method, amino protective groups which may be present can also be split off, depending on the hydrolysis conditions and the nature of the amino protective groups. The complete hydrolysis to a compound of the formula III and the subsequent introduction of an amino protective group can take place in one step. For example, a resulting methyl ester of a compound of the formula III, wherein the amino group is acylated with the trifluoroacetyl group, for example 2-(5-trifluoroacetaminomethyl-2-thienyl or -2-furanyl)-acetic acid methyl ester, can first be hydrolysed by treatment with a base, for example an alkali metal hydroxide, such as sodium hydroxide, in water or water and a water-miscible organic solvent, such as dioxane, and then be treated in the same reaction mixture with, for example, tert.-butoxycarbonyl azide, whereupon, following acidification and customary working up, 2-(5-tert.-butoxycarbonylaminomethyl-2-thienyl or -2-furanyl)-acetic acid can be obtained.

A compound of the formula III with an unprotected amino group can, however, also be isolated and one of the amino protective groups mentioned can then be introduced in accordance with any known method. Thus an acyl radical can be introduced as an amino protective group into the amino group, for example in accordance with the acylation process described above. Further, a triarylmethyl group can be introduced into the free amino group, for example by treatment with a reactive ester of the triarylmethanol, such as trityl chloride, preferably in the presence of a basic agent, such as pyridine.

An amino group can also be protected by introducing a silyl and stannyl group. Such groups are introduced in a manner which is in itself known, for example by treatment with a suitable silylating agent, such as a dihalogeno-di-lower alkyl-silane or tri-lower alkylsilyl halide, for example dichloro-dimethylsilane or trimethylsilyl chloride, or an optionally N-mono-lower alkylated, N,N-di-lower alkylated, N-tri-lower alkylsilylated or N-lower alkyl-N-tri-lower alkylsilylated N-(tri-lower alkyl-silyl)-amine (see, for example, British Pat. No. 1,073,530), or by treatment with a suitable stannylating agent, such as a bis-(tri-lower alkyl-tin)-oxide, for example bis-(tri-n-butyl-tin)-oxide, a tri-lower alkyl-tin hydroxide, for example triethyl-tin hydroxide, a tri-lower alkyl-lower alkoxy-tin compound, tetra-lower alkoxy-tin compound or tetra-lower alkyl-tin compound, and a tri-lower alkyl-tin halide, for example tri-n-butyl-tin chloride (see, for example, Netherlands Published Specification 67/11,107).

An amino group can also be protected by introducing a 2-carbonyl-1-vinyl group, whereby enamine or ketimine compounds are formed. Such groups can be obtained, for example, by treating the amine with a 1,3-dicarbonyl compound, for example with acetoacetic acid methyl ester or acetoacetic acid N,N-dimethylamide, in an anhydrous medium, for example a lower alkanol, such as methanol.

Arylthio or aryl-lower alkylthio, and also aryl-sulphonyl, protective groups can be introduced into an amino group by treatment with a corresponding alkylthio or aryl-lower alkylthio or arylsulphonyl halide, for example chloride.

The reactive functional acid derivatives of an acid of the formula III can be prepared in a manner which is in itself known. Acid halides are prepared, for example, by reacting a compound of the formula III, preferably having a protected amino group, or a salt thereof, with a halogenating agent, for example phosphorus pentachloride, thionyl chloride, isobutyl chloroformate or oxalyl chloride. The reaction is preferably carried out in a non-aqueous solvent or solvent mixture, such as a carboxylic acid amide, for example dimethylformamide, and/or a tertiary amine, such as a tri-lower alkylamine, for example triethylamine, or a tertiary cyclic amine, such as N-methyl-morpholine. The acid halide obtained does not have to be purified further but can be reacted direct with the amine of the formula II, and for this reaction the same solvents or solvent mixtures can be employed as are usable for the preparation of the acid halide.

Symmetrical anhydrides, or mixed anhydrides other than halides, of compounds of the formula III, preferably having a protected amino group, can be prepared, for example, by reacting a corresponding compound having a free carboxyl group, preferably a salt, especially an alkali metal salt, for example a sodium salt, or ammonium salt, for example triethylammonium salt, thereof, with a reactive derivative, such as a halide, for example the chloride, of one of the acids mentioned, for example a lower alkyl halogenoformate or a lower alkanecarboxylic acid chloride.

Activated esters of compounds of the formula III, preferably with a protected amino group, can be prepared, for example, by reacting a corresponding compound having a free carboxyl group with a phenol which is optionally substituted, for example by nitro or halogen, such as chlorine, such as, inter alia, a nitrophenol, for example 4-nitrophenol or 2,4-dinitrophenol, or a polyhalogenophenol, for example 2,3,4,5,6-pentachlorophenol, in the presence of a carbodiimide, for example one of the carbodiimides mentioned earlier, such as N,N'-dicyclohexylcarbodiimide.

In the process according to the invention and in additional measures which may have to be carried out, and also in the manufacture of the starting materials, it is possible, where necessary, temporarily to protect, in a manner which is in itself known, free functional groups which are present in the starting materials or in the compounds obtainable according to the process and do not participate in the reaction, for example free amino groups, for example by acylation, tritylation or silylation or free hydroxyl or mercapto groups, for example by etherification or esterification, and free carboxyl groups, for example by esterification, including silylation, and to liberate these functional groups again if desired, after the reaction has taken place, in a manner which is in itself known, for example by solvolysis or reduction, as described above.

The pharmacologically usable compounds of the present invention can be employed, for example, to manufacture pharmaceutical preparations which contain an active amount of the active substance together with, or mixed with, inorganic or organic, solid or liquid, pharmaceutically usable excipients which are suitable for enteral, or preferably, parenteral administration. Thus, tablets or gelatine capsules are used which contain the active compound together with diluents, for example lactose, dextrose, mannitol, sorbitol, cellulose and/or glycine, and lubricants, for example silica, talc, stearic acid or salts thereof, such as magnesium stearate or calcium stearate, and/or polyethylene glycol; tablets also contain binders, for example magnesium aluminium silicate, starches, such as corn starch, wheat starch, rice starch or arrowroot starch, gelatine, tragacanth, methylcellulose, sodium carboxylmethylcellulose and/or polyvinylpyrrolidone and, if desired, disintegrating agents, for example starches, agar, alginic acid or a salt thereof, such as sodium alginate, and/or effervescent mixtures, or adsorbents, dyestuffs, flavouring substances and sweeteners. Preferably, the pharmacologically active compounds of the present invention are used in the form of injectable, that is to say intravenously administrable, preparations, or of infusion solutions. Such solutions are preferably isotonic aqueous solutions or suspensions and these can also be prepared before use, for example from lyophilised preparations which contain the active substance by itself or together with an excipient, for example mannitol. The pharmaceutical preparations can be sterilised and/or contain auxiliaries, for example preservatives, stabilisers, wetting agents and/or emulsifiers, solubilising agents, salts for regulating the osmotic pressure and/or buffers. The pharmaceutical preparations in question which, if desired, can contain further pharmacologically valuable materials, are prepared in a manner which is in itself known, for example by means of conventional mixing, granulating, dragee-making, dissolving or lyophilising processes, and contain from about 0.1% to 100%, and in particular from about 1% to about 50%, of lyophilisate containing up to 100% of the active substance.

Unless defined otherwise, the term "lower" for example in lower alkyl, lower alkoxy and the like, denotes that the particular hydrocarbon group possesses up to 7, preferably up to 4, carbon atoms.

The examples which follow serve to illustrate the invention.

EXAMPLE 1

0.90 g of 2-(5-tert.-butoxycarbonylaminomethyl-2-thienyl)-acetic acid is dissolved in 20 ml of methylene chloride (distilled over phosphorus pentoxide) and 334 mg of N-methylmorpholine, the solution, from which moisture is excluded, is cooled to −20°C, and 0.45 ml of isobutyl chloroformate is added dropwise whilst keeping the temperature at between −15° and −20° C. After 30 minutes, a solution of 1.04 g of 7β-aminocephalosporanic acid diphenylmethyl ester in 5 ml of methylene chloride is added and the mixture is then stirred further for 2 hours at −10° C and 8 hours at room temperature. It is poured into ice-cold water, the pH is adjusted to 8.0 with dipotassium hydrogen phosphate and the mixture is repeatedly extracted with methylene chloride. The extracts are washed with sodium chloride solution and dried with magnesium sulphate, after which the solvent is removed under reduced pressure. The residue is crystallised from ether. 3-Acetoxymethyl-7β-[2-(5-tert.-butoxycarbonylaminomethyl-2-thienyl)-acetamino]-ceph-3-em-4-carboxylic acid diphenylmethylester, melting point 134°-136° C, is obtained. Thin layer chromatogram (silica gel; hexane/ethyl acetate/methanol, 20:40:40): Rf = 0.71, infrared absorption spectrum (Nujol): bands at $3.03\mu$; $5.68\mu$; $5.77\mu$; $6.02\mu$; $6.26\mu$ and $6.57\mu$; ultraviolet absorption spectrum (in ethanol): $\lambda_{max} = 245$ nm ($\epsilon = 15,100$).

A mixture of 1.80 g of the above 3-acetoxymethyl-7β-[2-(5-tert.-butoxycarbonylaminomethyl-2-thienyl)-acetylamino]-ceph-3-em-4-carboxylic acid diphenylmethyl ester, 5 ml of anisole and 20 ml of trifluoroacetic acid is stirred in a closed flask for 15 minutes at room temperature. The solution, with added toluene, is twice evaporated to dryness in vacuo. The residue is triturated with ether and filtered off. 1.2 g of a powder are obtained and are dissolved in 30 ml of 90% strength methanol. The solution is brought to pH 6 with a few drops of triethylamine/methanol (1:4) mixture and is allowed to crystallise at a low temperature (about 6° C). The 3-acetoxymethyl-7β-[2-(5-aminomethyl-2-thienyl)-acetylamino]-ceph-3-em-4-carboxylic acid which is obtained in a finely crystalline form is filtered off, washed with methanol and dried, melting point >200° C (decomposition); ultraviolet absorption spectrum (in 0.1 N hydrochloric acid): $\lambda_{max} = 243$ m$\mu$ ($\epsilon = 14,800$); infrared absorption spectrum (in mineral oil): bands at $3.02\mu$, $5.68\mu$, $5.77\mu$, $5.99\mu$, $6.13\mu$ and $6.52\mu$.

The starting material can be prepared as follows:

A solution of 20 g of thenylamine hydrochloride in a mixture of 100 ml of trifluoroacetic acid and 100 ml of acetic anhydride is stirred for 2 hours at 55° C, with exclusion of moisture. The reaction mixture is concentrated completely under reduced pressure, 50 ml of toluene are added and the mixture is again concentrated. The crude product is dissolved in ethyl acetate and the solution is treated with active charcoal, filtered through silica gel and concentrated under reduced pressure. After recrystallisation from ether, 2-acetyl-5-trifluoroacetylaminomethyl-thiophene of melting point 83°-84° C is obtained.

2-Acetyl-5-trifluoroacetaminomethyl-thiophene can also be prepared as follows:

8.0 ml of thiophene are added to a solution of 14.3 g of N-hydroxymethyltrifluoroacetamide in 25 ml of trifluoroacetic acid, the mixture is kept for 30 hours with exclusion of moisture, 100 ml of acetic anhydride are added and the whole is warmed to 65° C for 20 hours. Working up of the reaction mixture and purification of the resulting 2-acetyl-5-trifluoroacetylaminomethyl-thiophene are effected as in the case of the method which starts from 2- thenylamine hydrochloride.

40 ml of 70% strength perchloric acid are added to a solution of 34.2 g of thallium-(III) nitrate trihydrate in 100 ml of methanol whilst cooling with ice and a solution of 20 g of 2-acetyl-5-trifluoro-acetylamino-thiophene in 500 ml of methanol is added dropwise over the course of 15 minutes at +5° C under a nitrogen atmosphere. The solution is warmed to 50° C and is stirred at this temperature for 2½ hours. The reaction mixture is cooled to approx. +5° C and poured into an ice-cold solution of 120 g of dipotassium hydrogen phosphate in 300 ml of water. The mixture is filtered and the filter residue is washed with methanol. The filtrate is concentrated to approx. 300 ml under reduced pressure and is extracted three times with 150 ml of chloroform. The extracts are washed with water and subsequently with saturated sodium chloride solution, dried over magnesium sulphate and concentrated under a water pump vacuum. 2-(5-Trifluoroacetylaminomethyl-2-thienyl)-acetic acid methyl ester, boiling point 116°-120°C/0.02 mm Hg, remains.

In another experiment, a solution of 20 g of 2-acetyl-5-trifluoroacetylamino-thiophene in 500 ml of methanol was added dropwise over the course of 15 minutes to a solution of 35.5 g of thallium-(III) nitrate trihydrate in 100 ml of methanol under a nitrogen atmosphere. Further processing of the reaction mixture and isolation of the 2-(5-trifluoroacetylaminomethyl-2-thienyl)-acetic acid methyl ester are effected in an analogous manner.

Thin layer chromatogram (silica gel: toluene/ethyl acetate, 60:40): Rf = 0.65; infrared absorption spectrum (in methylene chloride): bands at 2.93µ, 3.39µ, 5.75µ and 5.80µ; ultraviolet absorption spectrum (in ethanol): $\lambda_{max} = 240$ nm ($\epsilon = 9.700$).

40 ml of 2 N sodium hydroxide solution are added to a solution of 9.7 g of 2-(5-trifluoroacetylaminomethyl-2-thienyl)-acetic acid methyl ester in 50 ml of dioxane at 20° C under a nitrogen atmosphere. The mixture is stirred for 2 hours at 20°–25° C and diluted with 50 ml of dioxane, and 8.5 ml of tert.-butoxycarbonyl azide are added to the solution, after which the mixture is stirred further for 16 hours at 20°–25° C. The reaction mixture is then cooled to approx. 5° C and the pH is adjusted to 2.5 with 20% strength phosphoric acid (approx. 40 ml). The mixture is concentrated under reduced pressure to approx. 50 ml and is extracted with three times 200 ml of ethyl acetate. The extracts are washed with sodium chloride solution, dried over magnesium sulphate, decolourised by treatment with Norit and concentrated. Recrystallisation from ether gives 2-(5-N-tert.-butoxycarbonylaminomethyl-2-thienyl)-acetic acid of melting point 114°–115° C. Thin layer chromatogram: (silica gel; chloroform/ethyl acetate/acetic acid, 80:19:1) Rf = 0.2; infrared absorption spectrum (in mineral oil): bands at 3.03µ, 5.84µ and 6.05µ; ultraviolet absorption spectrum (in ethanol): $\mu_{max} = 240$ nm ($\epsilon = 8,900$).

EXAMPLE 2

1.50 ml of triethylamine, 1.6 ml of N,N-dimethylaniline and 2,3 ml of trimethylchlorosilane are added to a stirred suspension of 2.13 g of 7β-amino-3-[(6-methyl-1-oxido-pyridazin-3-ylthio)-methyl]-ceph-3-em-4-carboxylic acid in 20 ml of methylene chloride at 20°–25° C. The mixture is warmed to 40° C over the course of 20 minutes, whilst stirring, and is then cooled to +5° C. At the same time, 1.95 g of 2-(5-tert.-butoxycarbonylaminomethyl-2-thienyl)-acetic acid are dissolved in 20 ml of methylene chloride, 0.05 ml of dimethylformamide and 5 ml of oxalyl chloride. The mixture is stirred for 30 minutes at the reflux temperature under a slight stream of nitrogen, the readily volatile constituents are distilled off in vacuo and the oily residue is dissolved in 10 ml of methylene chloride. This solution is added, at 5°–10° C, to the solution which contains the amine component which has now been silylated. This mixture is stirred for 2 hours at 10°–25° C and poured into water, the pH is adjusted to approx. 7 with sodium bicarbonate, the whole is extracted with methylene chloride and carefully acidified to approx. pH 2 with concentrated hydrochloric acid, and the precipitate formed is filtered off. It is repeatedly washed with water and after subsequent drying of the filter residue in a high vacuum over potassium hydroxide, 7β-[2-(5-tert.-butoxycarbonylaminomethyl-2-thienyl)-acetylamino]-3-[(6-methyl-1-oxido-pyridazin-3-yl-thio)-methyl]-ceph-3-em-4-carboxylic acid is obtained; thin layer chromatogram (silica gel; glacial acetic acid/water/butanol, 45:10:45): Rf = 0.58; infrared absorption spectrum (in mineral oil): bands at 5.63µ and 5.96µ.

3.7 g of 7β-[2-(5-tert.-butoxycarbonylaminomethyl-2-thienyl)-acetamino]-3-[(6-methyl-1-oxido-pyradazin-3-ylthio)-methyl]-ceph-em-4-carboxylic acid are dissolved in 30 ml. of trifluoroacetic acid and after 10 minutes the volatile constituents are removed in vacuo, with repeated addition of toluene. The residue is stirred with 50 ml of methanol, insoluble material is filtered off and the product is precipitated by adding triethylamine (until the pH is approx. 4.5). The mixture is filtered, the filter residue is washed with ether and dried, and 7β-[2-(5-aminomethyl-2-thienyl)-acetylamino]-3-[(6-methyl-1-oxidopyridazin-3-ylthio)-methyl]-ceph-em-4-carboxylic acid is thus obtained; melting point > 180° C (decomposition); ultraviolet absorption spectrum (in 0.01 N aqueous sodium bicarbonate solution): $\lambda_{max} = 235$ mµ ($\epsilon = 18,300$); 267 mµ ($\epsilon = 15,200$); and 338 mµ ($\epsilon = 4,250$); infrared absorption spectrum (in mineral oil): bands at 3.07µ, 5.63µ, 5.97µ and 6.52µ.

EXAMPLE 3

A mixture of 0.95 g of 7β-[2-(5-aminomethyl-2-thienyl)-acetylamino]-3-acetoxymethyl-ceph-3-em-4-carboxylic acid, 0.3 g. of 3-mercapto-6-methylpyridazine-1-oxide and 180 mg of sodium bicarbonate in 20 ml of water is warmed to 50° C for 24 hours, whilst stirring, treated with active charcoal and filtered. The filtrate is adjusted to pH 4.1 with acetic acid. The mixture is filtered and the filter residue is treated with methanol. The methanol-soluble component is purified as in Example 2. 7µ-[2-(5-aminomethyl-2-thienyl)-acetylamino]-3-[(6-methyl-1-oxido-pyridazin-3-ylthio)-methyl]-ceph-3-em-4-carboxylic acid, which according to spectroscopic data is identical with the product obtained according to the method of Example 2, is obtained.

EXAMPLE 4

1.87 g of 2-(5-tert.-butoxycarbonylaminomethyl-2-furyl)-acetic acid are dissolved in 200 ml of methylene chloride (distilled over phosphorus pentoxide) and 0.80 ml of N-methylmorpholine, the solution is cooled to −20° C whilst excluding moisture and 1.0 ml of isobutyl chloroformate is added dropwise whilst keeping the temperature at between −15° and −20° C. After 30 minutes, a solution of 2.31 g of 7β-amino-cephalosporanic acid diphenylmethyl ester in 10 ml of methylene chloride is added, and the mixture is then stirred further for 2 hours at −10° C and 8 hours at room temperature. It is poured into ice-cold water, the pH is adjusted to 8.0 with dipotassium hydrogen phosphate and the mixture is repeatedly extracted with methylene chloride. The extracts are washed with sodium chloride solution and dried with magnesium sulphate, after which the solvent is removed under reduced pressure. 3-Acetoxy-methyl-7µ-[2-(5-tert.-butoxycarbonylaminomethyl-2-furyl)-acetylamino]-ceph-3-em-4-carboxylic acid diphenylmethyl ester is obtained as a colourless foam which is employed as such for further conversion; thin layer chromatogram (silica gel; hexane/ethyl acetate/methanol, 20:40:40): Rf = 0.84.

A mixture of 3.70 g of the above 3-acetoxymethyl-7β-[2-(5-tert.-butoxycarbonylaminomethyl-2-furyl)-acetylamino]-ceph-3-em-4-carboxylic acid diphenylmethyl ester, 5 ml of anisole and 20 ml of trifluoroacetic acid is stirred in a closed flask for 15 minutes at room temperature. The solution, with addition of toluene, is twice evaporated to dryness in vacuo. The residue is triturated with ether, filtered off and dried for 12 hours in a high vacuum. 1.2 g of a powder are obtained and are dissolved in 30 ml of 90% strength methanol. The solution is brought to pH 6 with a few drops of triethylamine/methanol (1:4) mixture and is allowed to crystallise at a lower temperature (about 6° C). 3-Acetoxymethyl-7β-[2-(5-aminomethyl-2-furyl)-acetylamino]-ceph-3-em-4-carboxylic acid which is obtained in a finely crystalline form, is filtered off, washed with methanol and dried, melting point approx.

220° C (decomposition); ultraviolet absorption spectrum (in 0.1 N hydrochloric acid): $\lambda_{max} = 260$ m$\mu$ ($\epsilon = 9,700$); infrared absorption spectrum (in mineral oil): bands at 3.0$\mu$, 5.68$\mu$, 5.77$\mu$ and 6.04$\mu$; titrated equivalent weight: 411 (calculated: 409.42); pKx$_{MCS}$ = 8.57.

The starting material can be prepared as follows:

A mixture of 50 g of furfurylamine and 150 ml of trifluoroacetic anhydride is stirred for 2 hours at room temperature whilst excluding moisture. 150 ml of acetic acid are added and the reaction mixture is stirred further for 2 hours at 55° C. It is then concentrated completely under reduced pressure, 50 ml of toluene are added and the mixture is again concentrated. The crude product is dissolved in ethyl acetate and the solution is treated with active charcoal, filtered through silica gel and concentrated under reduced pressure. After recrystallisation from ether, 2-acetyl-5-trifluoroacetylaminoethyl-furane of melting point 99°–100° C is obtained. Ultraviolet absorption spectrum (in alcohol): 275 m$\mu$ ($\epsilon = 15,500$).

40 ml of 70% strength perchloric acid are added to a solution of 39.8 g of thallium-(III)nitrate trihydrate in 100 ml of methanol whilst cooling with ice and a solution of 20g of 2-acetyl-5-trifluoro-acetylaminofurane in 500 ml of methanol is added dropwise over the course of 15 minutes at +5° C under a nitrogen atmosphere. The solution is warmed to 50° C and stirred at this temperature for 2½ hours. The reaction mixture is cooled to approx. +5° C and poured into an ice-cold solution of 120 g of dipotassium hydrogen phosphate in 300 ml of water. The mixture is filtered and the filter residue is washed with methanol. The filtrate is concentrated to approx. 300 ml under reduced pressure and extracted three times with 150 ml of chloroform. The extracts are washed with water and subsequently with saturated sodium chloride solution, dried over magnesium sulphate and concentrated under a water pump vacuum. 2-(5-trifluoroacetylaminomethyl-2-furyl)-acetic acid methyl ester remains.

Thin layer chromatogram (silica gel; toluene/ethyl acetate, 60:40): Rf = 0.35. Infrared absorption spectrum (in methylene chloride): bands at 2.94$\mu$, 3.39$\mu$ and 5.80$\mu$.

The above reaction can also be carried out without addition of perchloric acid, in which case ice cooling to +5° C is not necessary.

75 ml of 2 N sodium hydroxide solution are added to a solution of 18.4 g of 2-(5-trifluoroacetylaminomethyl-2-furyl)-acetic acid methyl ester in 100 ml of dioxane at 20° C under a nitrogen atmosphere. The mixture is stirred for 4 hours at 20°–25° C and diluted with 100 ml of dioxane, and 34 ml of tert.-butoxycarbonyl azide are added to the solution, after which stirring is continued for 16 hours at 20°–25° C. The reaction mixture is cooled to approx. 5° C and the pH is adjusted to 2.5 with 20% strength phosphoric acid (approx. 40 ml). The whole is concentrated to approx. 100 ml under reduced pressure and is extracted with three times 200 ml of ethyl acetate. The extracts are washed with sodium chloride solution, dried over magnesium sulphae, decolourised by treatment with Norit and concentrated. Recrystallisation from ether gives 2-(5-N-tert.-butoxycarbonylaminomethyl-2-furyl)-acetic acid of melting point 72°–73° C.

EXAMPLE 5

1.5 ml of triethylamine, 1.6 ml of N,N-dimethylaniline and 2.3 ml of trimethylchlorosilane are added to a suspension of 2.0 g of 7-amino-3-(1-methyl-1H-tetrazol-5-ylthio)-methylceph-3-em-4-carboxylic acid in 60 ml of methylene chloride. The mixture is warmed to 40° C over the course of 20 minutes whilst stirring, and is then cooled to −10° C. A solution of 2-(5-tert.-butoxycarbonylaminomethyl-2-thienyl)-acetic acid chloride in 20 ml of methylene chloride, which has been prepared in the manner described in Example 2 from 1.95 g of 2(5-tert.-butoxycarbonylaminomethyl-2-thienyl)-acetic acid, is then added. The whole is stirred for 2 hours at 0°–25° C and poured into water, the mixture is adjusted to approx. pH 7 with sodium bicarbonate, extracted with methylene chloride and carefully acidified with concentrated hydrochloric acid and the precipitate formed is filtered off. The filter residue is washed with water and dried in vacuo at room temperature. The dried intermediate product is dissolved in 5 ml of trifluoroacetic acid whilst stirring and after 10 minutes the solution is concentrated in vacuo with repeated addition of toluene. The residue is stirred with 50 ml of methanol and filtered and the filtrate is adjusted to approx. pH 6 with triethylamine and left in a refrigerator for 2 hours. Filtration and washing of the filter residue with a little methanol and ether gives 7$\beta$-[2-(5-aminomethyl-2-thienyl)-acetylamino]-3-[(1-methyl-1H-tetrazol-5-ylthio)-methyl]-ceph-3-em-4-carboxylic acid; thin layer chromatogram (silica gel; acetonitrile/water, 4:1): Rf = 0.25; ultraviolet absorption spectrum (in 0.01 N aqueous sodium bicarbonate solution): $\lambda_{max} = 242$ m$\mu$ ($\epsilon = 14,100$); infrared absorption spectrum (in mineral oil): bands at 3.07$\mu$, 5.64$\mu$, 5.97$\mu$, 6.26$\mu$, 6.64$\mu$ etc.

EXAMPLE 6

3.28 g of 2-(5-N-tert.-butoxycarbonylaminomethyl-2-thienyl)-acetic acid are dissolved in 250 ml of methylene chloride and 1.33 ml of N-methylmorpholine. This solution is reacted analogously to Example 1, first with 1.58 ml of isobutyl chloroformate and then with a solution of 3.3 g of 7$\beta$-amino-3-methyl-ceph-3-em-4-carboxylic acid diphenylmethyl ester in 25 ml of methylene chloride, and is then worked up. After recrystallisation from ether, 3-methyl-7$\beta$-[2-(5-tert.-butoxycarbonylaminomethyl-2-thienyl)-acetamino]-ceph-3-em-4-carboxylic acid diphenylmethyl ester of melting point 138°–141° C is obtained; thin layer chromatogram (silica gel; toluene/ethyl acetate, 6:4) Rf = 0.48.

Using the process described in Example 1, 2.8 g of 3-methyl-7$\beta$-[2-(5-tert.-butoxycarbonylaminomethyl-2-thienyl)-acetamino]-ceph-3-em-4-carboxylic acid diphenylmethyl ester are converted into 3-methyl-7$\beta$-[2-(5-aminomethyl-2-thienyl)-acetylamino]-ceph-3-em-4-carboxylic acid by a treatment with 7 ml of anisole and 30 ml of trifluoroacetic acid and subsequent neutralisation with triethylamine in methanol. Infrared absorption spectrum (mineral oil): 2.88$\mu$, 3.17$\mu$, 3.80$\mu$, 5.69$\mu$, 6.02$\mu$, 6.40$\mu$ and 6.45$\mu$; ultraviolet absorption spectrum (ethanol): $\lambda_{max} = 243$ nm ($\epsilon = 11,200$); $\lambda_{max} = 219$ nm ($\epsilon = 6,900$).

EXAMPLE 7

A solution of 1.16 g of 3-acetoxymethyl-7$\beta$[2-(5-tert.-butoxycarbonylaminomethyl-2-thienyl)-acetylamino]-ceph-3-em-4-carboxylic acid and 0.185 g of sodium bicarbonate in 10 ml of water is added to a solution of 2.0 g of sodium thiobenzoate in 10 ml of water which is kept at 50° C. After 18 hours, the reaction mixture is diluted with water, acidified with 20% strength phosphoric acid and extracted with ethyl acetate. The extract is washed with sodium chloride solution, dried with magnesium sulphate and concentrated. The residue is triturated with petroleum ether and ether, filtered off and dried.

The filter residue is taken up in 3 ml of pyridine and 3 ml of dioxane and reacted with 2.1 ml of 40 percent strength mercury-(II) perchlorate solution and 1.0 ml of thiobenzoic acid. The mixture is warmed to 50° C for 1 hour, cooled and diluted with water and ethyl acetate, and the aqueous phase is separated off, treated with a basic ion exchanger and subsequently lyophilised. Thin layer chromatogram of the lyophilisate: Rf = 0.12 (butanol/glacial acetic acid/water, 45:45:10). The lyophilisate is treated with 1 ml of trifluoroacetic acid and after 15 minutes is again concentrated and dried. Neutralisation with triethylamine in water/methanol, filtration and drying gives 7β[2-(5-aminomethyl-2-thienyl)-acetylamino]-3-(1- pyridinio-methyl)-ceph-3-em-4-carboxylate, the structure of which is in accord with the spectroscopic data and in particular with the NMR spectrum: δ = 7.8 − 9.4

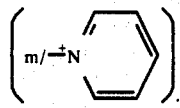

EXAMPLE 8

A solution of 4.89 g of 2-(tert.-butoxycarbonylaminomethyl-2-thienyl)-acetic acid in 90 ml of tetrahydrofurane is reacted with 2.5 ml of triethylamine and 2.35 ml of isobutyl chloroformate at −15° C. After 30 minutes, a solution of 4.68 g of 7β-aminocephalosporanic acid in 50 ml of tetrahydrofurane and 20 ml of water and 2.35 ml of triethylamine are added, the mixture is stirred for 1 hour at −5° C, the coolant is removed and the reaction is allowed to go to completion over the course of 2 hours. The reaction mixture is partially concentrated, acidified with 20 percent strength phosphoric acid and worked up with ethyl acetate. Cyclohexane is added to the concentrated extract until the mixture is slightly turbid and after some hours 3-acetoxymethyl-7β-[2-(5-tert.-butoxycarbonylaminomethyl-2-thienyl)-acetylamino]-ceph-3-em-4-carboxylic acid is filtered off. Thin layer chromatogram (silica gel; chloroform/ethyl acetate/glacial acetic acid, 80:19:1): Rf = 0.84. Ultraviolet absorption spectrum (alcohol): $\lambda_{max}$ = 244 mμ (ε = 14,200).

EXAMPLE 9

1 N sodium hydroxide solution is added to a suspension of 3.78 g of 3-acetoxymethyl-7β-[2-(5-tert.-butoxycarbonylaminomethyl-2-thienyl)-acetylamino]-ceph-3-em-4-carboxylic acid in 100 ml of water, whilst stirring, until the pH is 7.3. 5.0 g of cell lyophilisate of Bacillus subtilis, ATCC 6,633, are added and the reaction mixture is stirred at 35° C and kept at pH 7.4 by continuous addition of 1 N sodium hydroxide solution, until no further sodium hydroxide solution is consumed. The mixture is then covered with 300 ml of ethyl acetate and acidified to pH 2 with 20 percent strength phosphoric acid. The aqueous phase is separated off and extracted with 200 ml of ethyl acetate and the organic extracts are washed with sodium chloride solution, dried with sodium sulphate and reacted with 3.0 g of diphenyldiazomethane in 30 ml of dioxane. After 4 hours the mixture is concentrated and cyclohexane is added, after which 3-hydroxymethyl-7β-[2-(5-tert.-butoxycarbonylaminomethyl-2-thienyl)-acetylamino]-ceph-3-em-4-carboxylic acid diphenylmethyl ester is filtered off. Thin layer chromatogram (silica gel: toluene/acetone, 2:1) Rf = 0.32; ultraviolet absorption spectrum (alcohol) $\lambda_{max}$ = 243 mμ (ε = 13,600).

EXAMPLE 10

A solution of 3.45 g of 3-hydroxymethyl-7β-[2-(5-tert.-butoxycarbonylaminomethyl-2-thienyl)-acetylamino]-ceph-3-em-4-carboxylic acid diphenylmethyl ester in 60 ml of acetone is reacted with 1.40 g of trichloroacetyl isocyanate. After 2 hours, the mixture is diluted with 50 ml of water and concentrated to approx. 50 ml in vacuo. It is extracted with ethyl acetate and the extracts are concentrated and chromatographed on silica gel which has beforehand been deactivated with 5% of water, ethyl acetate being used as the migrating agent. The material evaporated in vacuo [thin layer chromatogram (silica gel; toluene/acetone, 2:1): Rf = 0.57] is reacted with 4 ml of trifluoroacetic acid and 2.5 ml of anisole at 0° C. The reaction mixture is concentrated, dried for 10 hours in a high vacuum and taken up in 5 ml of methanol, and the pH is adjusted to 6.0 with triethylamine. The mixture is then diluted with ether and after 2 hours 3-carbamoyloxymethyl-7β[2-(5-aminomethyl-2-thienyl)-acetylamino]-ceph-3-em-4-carboxylic acid is filtered off. Ultraviolet absorption spectrum (0.01 N hydrochloric acid):$\lambda_{max}$ = 243 mμ (ε = 14,100), melting point > 250° (decomposition). The obtained inner salt can be transformed into the corresponding water soluble sulfate hydrate by filtering it through a column of ion exchanger XAD-2 with aqueous sulfuric acid of pH 2.7 and lyophilizing the filtrate.

EXAMPLE 11

4,0 g of 2-(5-tert.-butoxycarbonylaminomethyl-2-thienyl)-acetic acid are dissolved in 200 ml of methylene chloride containing 1.65 ml of N-methylmorpholine, the solution, from which moisture is excluded, is cooled to −20° C and 1.95 ml of isobutyl chloroformate is added dropwise. After 30 minutes, a solution of 5.16 of 7β-amino-3-(5-methyl-1,3,4-thiadiazol-2-ylthiomethyl)-3-cephem-4-carboxylic acid and 7.20 ml of N,O-bis-trimethylsilyl-acetamid in 150 ml of methylene chloride is added dropwise, whereupon the reaction mixture is stirred further for one hour at −20° C and during 4 hours under slow warming up to room temperature, and is then narrowed down under reduced pressure. The residue is dissolved in water through addition of sodium hydrogen carbonate until a pH value of 8 is reached. The aqueous solution is washed with ethyl acetate, separated, acidified with 20% strength aqueous phosphoric acid until pH 2 and then extracted with ethyl acetate. The organic extract is washed with saturated aqueous sodium chloride solution, dried over magnesium sulfate and narrowed down. 7β-[2-(5-tert.-Butoxycarbonylaminomethyl-2-thienyl)-acetylamino]-3-(5-methyl-1,3,4-thiadiazol-2-yldithiomethyl)-3-cephem-4-carboxylic acid is thus obtained; thin layer chromatogram (silica gel): Rf = 0.40 (system: n-butanol/acetic acid/water 45:45:10), ultraviolet absorption spectrum (ethanol): $\lambda_{max}$ = 244 mμ (ε =

16'900); infrared absorption spectrum (in mineral oil): characteristic bands at 2.93 μ, 5.60 μ, 5.90 μ, 6.55 μ.

A mixture of 6.1 g of dicyclohexylcarbodiimide, 2.1 g of tert.-butanol and 0,06 g of cuprous-(I)-chloride is stirred during 5 days at room temperature. The suspension of O-tert.-butyl-N,N'-dicyclohexyl isourea so obtained is diluted with 30 ml of methylene chloride and added to a solution, kept at room temperature, of 2.0 g of 7β-[2-(5-tert.-butoxycarbonylaminomethyl-2-thienyl)-acetylamino]-3-(5-methyl-1,3,4-thiadiazol-2-ylthiomethyl)-3-cephem-4-carboxylic acid in 50 ml methylene chloride. It is filtered after 5 hours and the filtrate is narrowed down under reduced pressure. The residue is chromatographed on 40 g of silica gel, whereby with ethyl acetate the 7β-[2-(5-tert.-butoxycarbonylaminomethyl-2-thienyl)-acetylamino]-3-(5-methyl-1,3,4-thiadiazol-2-ylthiomethyl)-3-cephem-4-carboxylic acid tert.-butyl ester is eluated; thin layer chromatogram (silica gel): Rf = 0.70 (n-butanol/acetic acid/water 45:45:10).

A solution of 2.0 g of 7β-[2-(5-tert.-butoxycarbonylaminomethyl-2-thienyl)-acetylamino]-3-(5-methyl-1,3,4-thiadiazol-2-ylthiomethyl)-3-cephem-4-carboxylic acid in 20 ml of trifluoroacetic acid is left to stand under exclusion of moisture during 30 minutes at room temperature, and is then evaporated on addition of toluene under a water pump vacuum. The residue is triturated with diethyl ether and the trifluoroacetic acid salt of 7β-[2-(5-aminomethyl-2-thienyl)-acetylamino]-3-(5-methyl-1,3,4-thiadiazol-2-ylthiomethyl)-3-cephem-4-carboxylic acid thus obtained is dried under high vacuum at room temperature and is then dissolved in 20 ml of water. The aqueous solution is washed with ethyl acetate, brought to a pH-value of 6 with triethyl amine, and is narrowed down under a water pump vacuum to a volume of about 5 ml. The residue is diluted by dropwise addition of 30 ml of acetone, left to stand for 2 hours at 4° C and the precipitate is filtered off. The latter is washed with acetone and dried under high vacuum at room temperature: the inner walt of 7β-[2-(5-aminomethyl-2-thienyl)-acetylamino]-3-(5-methyl-1,3,4-thiadiazol-2-ylthiomethyl)-3-cephem-4-carboxylic acid, melting point 183° C (decomposition); thin layer chromatogram (silica gel): Rf = 0.13 (system: n-butanol/acetic acid/water 45:45:10); ultra violet absorption spectrum (0.1-n-aqueous sodium hydrogen carbonate soluton): $\lambda_{max}$ = 242 mμ (ε = 17000); infrared absorption spectrum (in mineral oil): characteristic bands at 5.68 μ, 6.04 μ, 6.34 μ, 6.49 μ, is obtained.

EXAMPLE 12

By reaction of 3-acetoxymethyl-7β-[2-(5-tert.-butoxycarbonylaminomethyl-2-thienyl)-acetylamino]-ceph-3-em-4-carboxylic acid in aqueous solution at pH ca. 7 with methyl mercaptan at 70°–80° C in an autoclave, the 3-methyl-thiomethyl-7β-[2-(5-tert.-butoxycarbonylaminomethyl-2-thienyl)-acetylamino]-ceph-3-em-4-carboxylic acid is obtained, which can be transformed according to Example 9, with diphenyl-diazomethane into the 3-methylthiomethyl-7β-[2-(5-tert.-butoxycarbonylaminomethyl-2-thienyl)-acetylamino]-ceph-3-em-4-carboxylic acid diphenylmethyl ester. Thereof can be prepared by treatment with trifluoroacetic acid and anisole, according to Example 10, the 3-methylthiomethyl-7β-[2-(5-aminomethyl-2-thienyl)-acetylamino]-ceph-3-em-4-carboxylic acid; melting point (after recrystallisation from ethanol): >280° C (decomposition; $\alpha_D^{20}$ = 105° ± 1° (c = 0.120, in 0.1 N hydrochloric acid), UV-spectrum (0.1 N hydrochloric acid; $\lambda_{max}$ = 245 mμ (ε = 14'800), shoulder at about 269 mμ (ε = 17'680); IR-spectrum (nujol): characteristic bands at 3.07; 3.30; 5.73; 6.03; 6.38; 6.51; 7.45; 8.10; 8.89; 9.06; 12.63 μ.

EXAMPLE 13

The starting material is prepared as follows: A solution of 4.08 g of 2-(5-tert.-butyloxycarbonylaminomethyl-2-thienyl)-acetic acid in 200ml of methylene chloride containing 1.65 ml of 4-methylmorpholine is cooled to −20° under exclusion of moisture and treated dropwise with 1.95 ml of chloroformic acid isobutyl ester. After 30 minutes a solution of 5.16 g of 7β-amino-3-(5-methyl-1,3,4-thiadiazol-2-ylthiomethyl)-3-cephem-4-carboxylic acid and 7.20 ml N,O-bis-(trimethylsilyl)-acetic acid amide in 150 ml of methylene chloride is added, whereupon the reaction mixture is stirred during one hour at −20° and during four hours while the temperature is allowed to slowly rise to room temperature and is then evaporated under reduced pressure. The residue is dissolved in water with the addition of sodium hydrogen carbonate until the pH reaches 8. The solution is washed with ethyl acetate, the separated aqueous layer is acidified to pH 2 with aqueous phosphoric acid of 20% strength and is extracted with ethyl acetate. The organic extract is washed with a saturated aqueous sodium chloride solution, dried over magnesium sulfate and evaporated under reduced pressure. One thus obtains the 7β-[2-(5-tert.-butyloxycarbonylaminomethyl-2-thienyl)-acetylamino]-3-(5-methyl-1,3,4-thiadiazol-2-ylthiomethyl)-3-cephem-4-carboxylic acid; thin layer chromatogram (silicagel): Rf = 0,40 (system: n-butanol/acetic acid/water45:45:10), ultraviolet absorption spectrum (ethanol): $\lambda_{max}$ 244 mμ (ε = 16900); infrared absorption spectrum (in mineral oil): characteristic bonds at 2,93 μ, 5,60 μ, 5,90 μ, and 6.55 μ.

A mixture of 6,1 g of dicyclohexylcarbodiimide, 2,1 g of tert.-butanol and 0,06 g a copper-(I)-chloride is stirred for five days at room temperature. The resulting suspension of the O-tert.-butyl-N,N'-dicyclohexyl-isourea is diluted with 30 ml of methylene chloride and added to a solution of 2,0 g of 7β-[2-(5-tert.-butyloxycarbonylaminomethyl-2-thienyl)-acetylamino]-3-(5-methyl-1,3,4-thiadiazol-2-ylthiomethyl)-3-cephem-4-carboxylic acid in 50 ml methylene chloride, kept at room temperature. After five hours the reaction mixture is filtered and the filtrate is evaporated under reduced pressure. The residue is chromatographed using 40 g of silicagel; with ethyl acetate the 7β-[2-(5-tert.-butyloxycarbonylaminomethyl-2-thienyl)-acetylamino]-3-(5-1,3,4-thiadiazol-2-ylthiomethyl)-3-cephem-4-carboxylic acid tert.-butyl ester is eluted; thin layer chromatogram (silicagel): Rf = 0,70 (n-butanol/acetic acid/water 45:45:10).

EXAMPLE 14

Dry ampoules or phials, containing 0.5 g of 3-acetoxymethyl-7β-[2-(5-aminomethyl-2-thienyl)-acetamino]-ceph-3-em-4-carboxylic acid are manufactured as follows:

| Composition (for 1 ampoule or phial) | |
|---|---|
| 3-Acetoxymethyl-7β-[2-(5-aminomethyl-2-thienyl)-acetamino]-ceph-3-em-4-carboxylic acid | 0.5 g |
| Mannitol | 0.05 g |

A sterile aqueous solution of the 3-acetoxymethyl-7β-[2-(5-aminomethyl-2-thienyl)-acetamino]-ceph-3-em-4-carboxylic acid and the mannitol is sealed in 5 ml ampoules or 5 ml phials under aseptic conditions and tested.

EXAMPLE 15

Dry ampoules or phials, containing 0.5 g of 7β-[2-(5-aminomethyl-2-thienyl)-acetamino]-3-[(6-methyl-1-oxido-pyridazin-3-ylthio)-methyl]-ceph-3-em-4-carboxylic acid are manufactured as follows:

| Composition (for 1 ampoule or phial) | |
|---|---|
| 7β-[2-(5-Aminomethyl-2-thienyl)-acetamino]-3-[(6-methyl-1-oxido-pyridazin-3-ylthio)-methyl]-ceph-3-em-4-carboxylic acid | 0.5 g |
| Mannitol | 0.05 g |

A sterile aqueous solution of the 7β-[2-(5-aminomethyl-2-thienyl)-acetamino]-3-[(6-methyl-1-oxido-pyridazin-3-ylthio)-methyl]-ceph-3-em-4-carboxylic acid and the mannitol is subjected to freeze-drying in 5 ml ampoules or 5 ml phials under aseptic conditions, and the ampoules or phials are sealed and tested.

We claim:

1. A compound of the formula

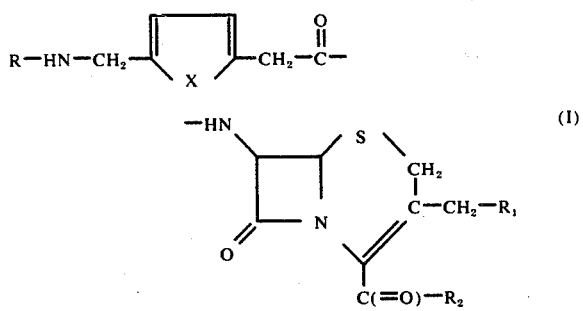

wherein X denotes sulphur or oxygen, R denotes hydrogen or an amino protective group, $R_1$ denotes a radical $-S-R_4$, wherein $R_4$ is tetrazolyl, thiadiazolyl or tetrazolyl or thiadiazolyl substituted by lower alkyl, or a radical $-S-R_5$, wherein $R_5$ is N-oxido-pyridazinyl or N-oxido-pyridazinyl substituted by lower alkyl, and $R_2$ denotes hydroxyl or a carboxyl protective radical which together with the carbonyl grouping of the formula $-C(=O)-$ forms a protected carboxyl group, and their therapeutically acceptable salts.

2. A compound of the formula I according to claim 1, wherein X represents oxygen or sulphur, R denotes hydrogen, lower alkoxycarbonyl which on the carbon atom in α-position to the oxy group carries several aliphatic substituents or is branched, a methoxycarbonyl group substituted by benzoyl, β-halogenoalkoxycarbonyl, phenyl-lower alkoxycarbonyl, phenyl-lower alkoxycarbonyl substituted by lower alkyl, hydroxy, lower alkoxy or nitro, diphenylmethoxycarbonyl, benzyl, triphenylmethyl or diphenylmethoxycarbonyl or benzyl or triphenylmethyl substituted by lower alkoxy, $R_1$ represents a radical of the formula $-S-R_4$, wherein $R_4$ represents tetrazolyl, thiadiazolyl or tetrazolyl or thiadiazolyl substituted by lower alkyl, or a radical of the formula $-S-R_5$, wherein $R_5$ is N-oxido-pyridazinyl or N-oxido-pyridazinyl substituted by lower alkyl, and $R_2$ represents hydroxyl, tri-lower alkylsilyloxy, lower alkoxy branched at the α-position or substituted in the α-position by phenyl, phenyl substituted by lower alkoxy or nitro or benzoyl or substituted in the β-position by halogen, and their therapeutically acceptable salts.

3. A compound of the formula I

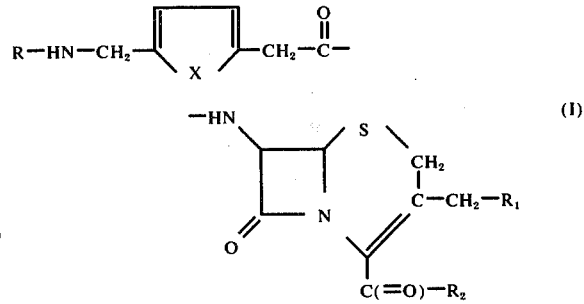

wherein X is oxygen or sulphur, R denotes hydrogen, tert.-butoxycarbonyl, tert.-pentoxycarbonyl, phenacyloxycarbonyl, 2,2,2-trichloroethoxycarbonyl, 2-iodoethoxycarbonyl, benzyloxy- or 4-nitrobenzyloxycarbonyl, diphenylmethoxycarbonyl, 4,4'-dimethoxydiphenylmethoxycarbonyl, benzyl, p-methoxybenzyl or trityl, $R_1$ denotes a radical $-S-R_4$, wherein $R_4$ is tetrazolyl, thidiazolyl, 1-methyl-1H-tetrazol-5-yl or 5-methyl-1,3,4-thiadiazol-2-yl, or a radical $-S-R_5$, wherein $R_5$ is N-oxido-pyridazinyl or 6-methyl-1-oxido-pyridazin-3-yl, and $R_2$ is hydroxy, trimethylsilyloxy, tert.-butoxy, benzyloxy, 4-methoxybenzyloxy, 4-nitrobenzyloxy, diphenylmethoxy, 4,4'-dimethoxydiphenylmethoxy, phenacyl, 2,2,2-trichloroethoxy or 2-iodoethoxy, and their therapeutically acceptable salts.

4. A compound as claimed in claim 3 being 7β-[2-(5-tert.-butoxycarbonylaminomethyl-2-thienyl)-acetylamino]-3-[(1-methyl-1H-tetrazol-5-ylthio)-methyl]-ceph-3-em-4-carboxylic acid diphenylmethyl ester or a therapeutically acceptable salt thereof.

5. A compound as claimed in claim 3 being 7β-[2-(5-aminomethyl-2-thienyl)-acetylamino]-3-[(1-methyl-1H-tetrazol-5-ylthio)-methyl]-ceph-3-em-4-carboxylic acid or a therapeutically acceptable salt thereof.

6. A compound as claimed in claim 3 being 7β-[2-(5-aminomethyl-2-thienyl)-acetylamino]-3-[(5-methyl-1,3,4-thiadiazol-2-ylthio)-methyl]-ceph-3-em-4-carboxylic acid or a therapeutically acceptable salt thereof.

7. A compound as claimed in claim 3 being 7β-[2-(5-aminomethyl-2-thienyl)-acetylamino]-3-[(6-methyl-1-oxido-pyridazin-3-ylthio)-methyl]-ceph-3-em-4-carboxylic acid or a therapeutically acceptable salt thereof.

8. An antibiotic pharmaceutical composition comprising a therapeutically effective amount of a compound as claimed in claim 3 together with a pharmaceutical carrier.

* * * * *